(12) United States Patent
Luo et al.

(10) Patent No.: US 8,748,429 B2
(45) Date of Patent: Jun. 10, 2014

(54) CGRP RECEPTOR ANTAGONISTS

(75) Inventors: Guanglin Luo, Madison, CT (US);
Gene M. Dubowchik, Middlefleid, CT (US); John E. Macor, Guilford, CT (US); Ling Chen, Middletown, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 54 days.

(21) Appl. No.: 13/439,096

(22) Filed: Apr. 4, 2012

(65) Prior Publication Data
US 2013/0096130 A1 Apr. 18, 2013

Related U.S. Application Data

(60) Provisional application No. 61/474,567, filed on Apr. 12, 2011.

(51) Int. Cl.
| A61K 31/495 | (2006.01) |
| A01N 43/50 | (2006.01) |
| A01N 43/54 | (2006.01) |
| A01N 43/56 | (2006.01) |
| A01N 43/58 | (2006.01) |

(52) U.S. Cl.
USPC ........... 514/249; 514/277; 514/279; 514/299; 514/359; 514/365; 514/366; 514/367; 544/349

(58) Field of Classification Search
USPC ......... 514/249, 277, 279, 299, 303, 359, 365, 514/366, 367, 372, 373, 374, 375, 408, 514/423; 544/349
See application file for complete search history.

(56) References Cited

U.S. PATENT DOCUMENTS 8,044,043 B2 * 10/2011 Luo ............................... 514/221
8,314,117 B2 * 11/2012 Luo et al. ...................... 514/278

* cited by examiner

Primary Examiner — My-Chau T Tran
(74) Attorney, Agent, or Firm — James Epperson

(57) ABSTRACT

The disclosure generally relates to the novel compounds of formula I, including pharmaceutically acceptable salts, which are CGRP receptor antagonists. The disclosure also relates to pharmaceutical compositions and methods for using the compounds in the treatment of CGRP related disorders including migraine and other headaches, neurogenic vasodilation, neurogenic inflammation, thermal injury, circulatory shock, flushing associated with menopause, airway inflammatory diseases such as asthma, and chronic obstructive pulmonary disease (COPD).

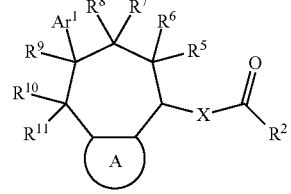

14 Claims, No Drawings

CGRP RECEPTOR ANTAGONISTS

CROSS REFERENCE TO RELATED APPLICATIONS

This patent application claims the benefit of U.S. provisional patent application No. 61/474,567 filed Apr. 12, 2011.

BACKGROUND OF THE INVENTION

The disclosure generally relates to the novel compounds of formula I, including pharmaceutically acceptable salts, which are CGRP-receptor antagonists. The disclosure also relates to pharmaceutical compositions and methods for using the compounds in the treatment of CGRP related disorders including migraine headaches, neurogenic vasodilation, neurogenic inflammation, thermal injury, circulatory shock, flushing associated with menopause, airway inflammatory diseases such as asthma, and chronic obstructive pulmonary disease (COPD).

Calcitonin gene-related peptide (CGRP) is a naturally occurring 37-amino-acid peptide first identified in 1982 (Amara, S. G. et al, Science 1982, 298, 240-244). Two forms of the peptide are expressed (αCGRP and βCGRP) which differ by one and three amino acids in rats and humans, respectively. The peptide is widely distributed in both the peripheral (PNS) and central nervous system (CNS), principally localized in sensory afferent and central neurons, and displays a number of biological effects, including vasodilation.

When released from the cell, CGRP binds to specific cell surface G protein-coupled receptors and exerts its biological action predominantly by activation of intracellular adenylate cyclase (Poyner, D. R. et al, Br J Pharmacol 1992, 105, 441-7; Van Valen, F. et al, Neurosci Lett 1990, 119, 195-8.). Two classes of CGRP receptors, CGRP1 and CGRP2, have been proposed based on the antagonist properties of the peptide fragment CGRP(8-37) and the ability of linear analogues of CGRP to activate CGRP2 receptors (Juaneda, C. et al. TiPS 2000, 21, 432-438). However, there is lack of molecular evidence for the CGRP2 receptor (Brain, S. D. et al, TiPS 2002, 23, 51-53). The CGRP1 receptor has three components: (i) a 7 transmembrane calcitonin receptor-like receptor (CRLR); (ii) the single transmembrane receptor activity modifying protein type one (RAMP1); and (iii) the intracellular receptor component protein (RCP) (Evans B. N. et al., J Biol Chem. 2000, 275, 31438-43). RAMP1 is required for transport of CRLR to the plasma membrane and for ligand binding to the CGRP-receptor (McLatchie, L. M. et al, Nature 1998, 393, 333-339). RCP is required for signal transduction (Evans B. N. et al., J Biol Chem. 2000, 275, 31438-43). There are known species-specific differences in binding of small molecule antagonists to the CORP-receptor with typically greater affinity seen for antagonism of the human receptor than for other species (Brain, S. D. et al, TiPS 2002, 23, 51-53). The amino acid sequence of RAMP1 determines the species selectivity, in particular, the amino acid residue Trp74 is responsible for the phenotype of the human receptor (Malice et al. J Biol Chem 2002, 277, 14294-8).

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. CNS Drugs 2001; 15(10): 745-53; Williamson, D. J. Microsc. Res. Tech. 2001, 53, 167-178.; Grant, A. D. Brit. J. Pharmacol. 2002, 135, 356-362.). Serum levels of CGRP are elevated during migraine (Goadsby P J, et al. Ann Neurol 1990; 28:183-7) and treatment with anti-migraine drugs returns CGRP levels to normal coincident with alleviation of headache (Gallai V. et al. Cephalalgia 1995; 15: 384-90). Migraineurs exhibit elevated basal CORP levels compared to controls (Ashina M, et al., Pain 2000, 86(1-2):133-8, 2000). Intravenous CORP infusion produces lasting headache in migraineurs (Lassen L H, et al. Cephalalgia 2002 February; 22(1):54-61). Preclinical studies in dog and rat report that systemic CORP blockade with the peptide antagonist CGRP(8-37) does not alter resting systemic hemodynamics nor regional blood flow (Shen, Y-T. et al, J Pharmacol Exp Ther 2001, 298, 551-8). Thus, CGRP-receptor antagonists may present a novel treatment for migraine that avoids the cardiovascular liabilities of active vasoconstriction associated with non-selective 5-HT1B/1D agonists, 'triptans' (e.g., sumatriptan).

CGRP antagonists have shown efficacy in human clinical trials. See Davis C D, Xu C. Curr Top Med. Chem. 2008 8(16):1468-79; Benemei S, Nicoletti P, Capone J G, Geppetti P. *Curr Opin Pharmacol.* 2009 9(1):9-14. Epub 2009 Jan. 20; Ho T W, Ferrari M D, Dodick D W, Galet V, Kost J, Fan X, Leibensperger H, Froman S, Assaid C, Lines C, Koppen H, Winner P K. *Lancet.* 2008 372:2115. Epub 2008 Nov. 25; Ho T W, Mannix L K, Fan X, Assaid C, Furtek C, Jones C J, Lines C R, Rapoport A M; *Neurology* 2008 70:1304. Epub 2007 Oct. 3.

CGRP receptor antagonists have been disclosed in PCT publications WO 2004/092166, WO 2004/092168, WO 2007/120590, and WO2009/126530.

The invention provides technical advantages, for example, the compounds are novel and inhibit CGRP. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses a series of CORP antagonist compounds including pharmaceutically acceptable salts, compositions, methods of making them, and methods of using them in therapeutic treatment.

One aspect of the invention is a compound of formula I

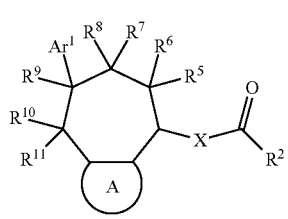

I such that ring A is selected from the group consisting of

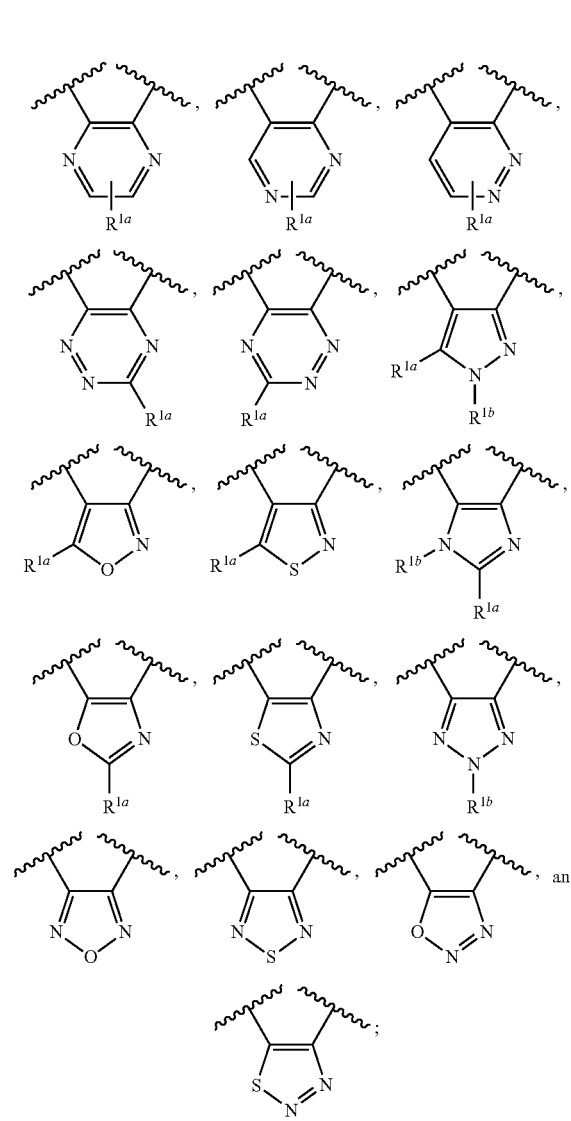

and wherein
$R^{1a}$ is hydrogen, cyano, halo, alkyl, haloalkyl, alkoxy, amino, alkylamino, dialkylamino, azetidinyl, pyrrolidinyl, or piperidinyl;
$R^{1b}$ is hydrogen, alkyl, or haloalkyl;
$R^2$ is piperidinyl substituted with 1 substituent selected from the group consisting of

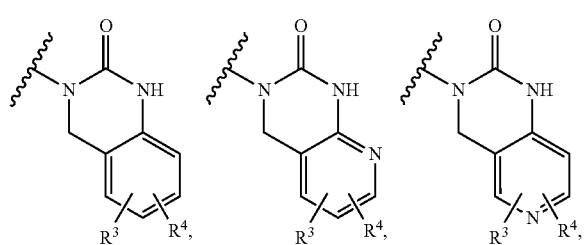

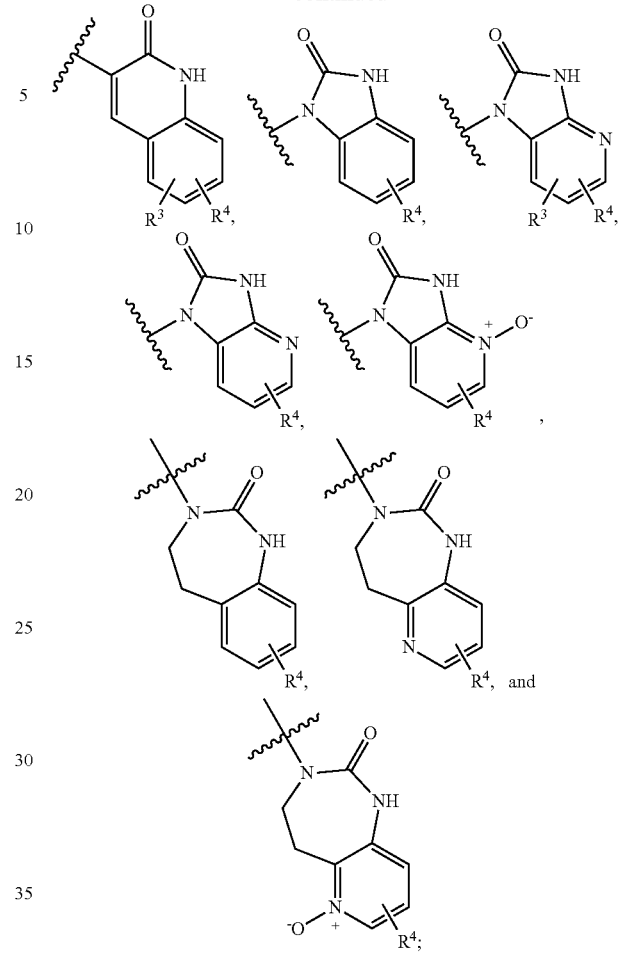

or $R^2$ is

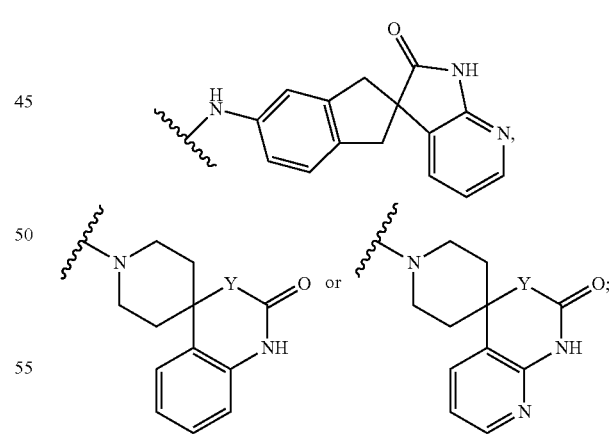

$R^3$ is hydrogen, halo, cyano, alkyl, haloalkyl, alkoxy, or haloalkoxy;
$R^4$ is hydrogen, halo, cyano, alkyl, haloalkyl, alkoxy, or haloalkoxy;
$R^5$ is hydrogen, hydroxy, alkoxy, haloalkoxy, azido, amino, alkylamino, or dialkylamino;
$R^6$ is hydrogen, hydroxy, alkoxy, haloalkoxy, azido, amino, alkylamino, or dialkylamino;

$R^7$ is hydrogen, hydroxy, alkoxy, haloalkoxy, azido, amino, alkylamino, or dialkylamino;
$R^8$ is hydrogen, hydroxy, alkoxy, haloalkoxy, azido, amino, alkylamino, or dialkylamino;
$R^9$ is hydrogen, hydroxy, alkoxy, haloalkoxy, azido, amino, alkylamino, or dialkylamino;
$R^{10}$ is hydrogen, hydroxy, alkoxy, haloalkoxy, azido, amino, alkylamino, dialkylamino, azetidinyl, pyrrolidinyl, piperidinyl, piperazinyl, morpholinyl, alkoxycarbonylamino, or benzyloxycarbonylamino;
$R^{11}$ is hydrogen, hydroxy, alkoxy, haloalkoxy, azido, amino, alkylamino, dialkylamino, azetidinyl, pyrrolidinyl, piperidinyl, piperazinyl, morpholinyl, alkoxycarbonylamino, or benzyloxycarbonylamino;
or $R^{10}$ and $R^{11}$ taken together is O or N—OH;
provided that at least one of $R^5$, $R^6$, $R^7$, $R^8$, $R^9$, $R^{10}$, or $R^{11}$ is not hydrogen;
$Ar^1$ is phenyl substituted with 0-3 substituents selected from the group consisting of cyano, halo, alkyl, haloalkyl, alkoxy, haloalkoxy, and alkylSO$_2$;
X is O, CH$_2$, or NH; and
Y is a bond, O, CH$_2$, or NH;
or a pharmaceutically acceptable salt thereof.

Another aspect of the invention is a compound of formula I with the designated stereochemistry.

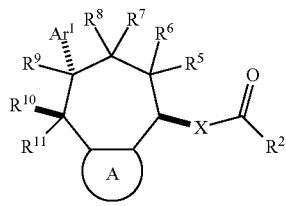

Another aspect of the invention is a compound of formula I where
$R^{1a}$ x is hydrogen, alkyl, or haloalkyl;
$R^{1b}$ is hydrogen or alkyl;
$R^2$ is piperidinyl substituted with 1 substituent selected from the group consisting of

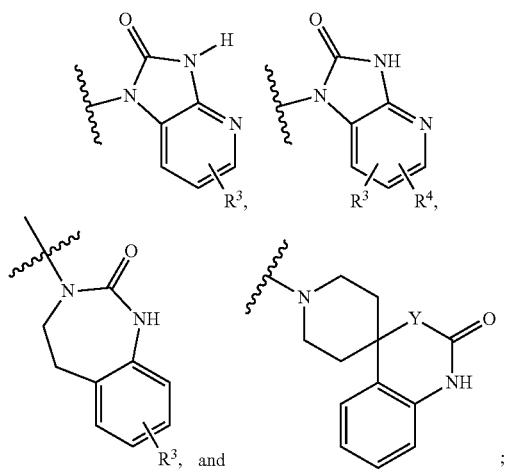

$R^3$ is hydrogen or halo;
$R^4$ is hydrogen or halo;
$R^5$ is hydrogen or hydroxy;
$R^6$ is hydrogen;
$R^7$ is hydrogen;
$R^8$ is hydrogen;
$R^9$ is hydrogen or hydroxy;
$R^{10}$ is hydroxy, alkoxy, haloalkoxy, azido, amino, alkylamino, dialkylamino, azetidinyl, pyrrolidinyl, piperidinyl, piperazinyl, morpholinyl, alkoxycarbonylamino, or benzyloxycarbonylamino;
$R^{11}$ is hydrogen;
or $R^{10}$ and $R^{11}$ taken together is oxo;
provided that at least one of $R^5$, $R^6$, $R^7$, $R^8$, $R^9$, or $R^{11}$ is not hydrogen;
$Ar^1$ is phenyl substituted with 0-2 halo substituents;
X is O, CH$_2$, or NH; and
Y is O;
or a pharmaceutically acceptable salt thereof.

Another aspect of the invention is a compound of formula I where $R^{1a}$ is hydrogen or haloalkyl; $R^{1b}$ is hydrogen; $R^2$ is piperidinyl substituted with 1 substituent selected from the group consisting of

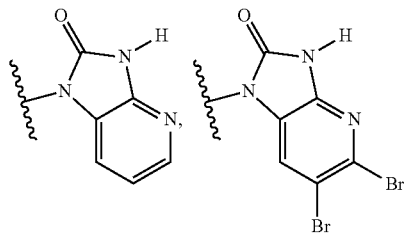

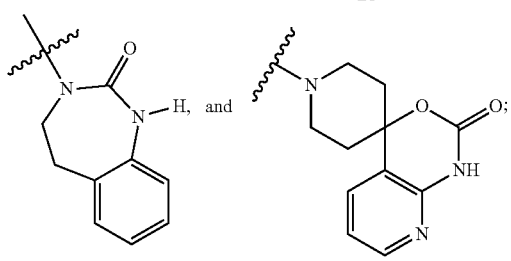

$R^5$ is hydrogen or hydroxy; $R^6$ is hydrogen; $R^7$ is hydrogen; $R^8$ is hydrogen; $R^9$ is hydrogen or hydroxy; $R^{10}$ is hydroxy, azido, amino, or alkoxycarbonylamino; $R^{11}$ is hydrogen; or $R^{10}$ and $R^{11}$ taken together is oxo; provided that at least one of $R^5$, $R^6$, $R^7$, $R^8$, $R^9$, or $R^{11}$ is not hydrogen; $Ar^1$ is phenyl or difluorophenyl; X is O, CH$_2$, or NH; and Y is O; or a pharmaceutically acceptable salt thereof.

Another aspect of the invention is a compound of formula I where ring A is

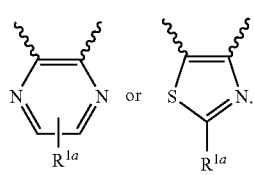

Another aspect of the invention is a compound of formula I where $R^2$ is N-piperidinyl and is 4-substituted.

Another aspect of the invention is a compound of formula I where the substituent is

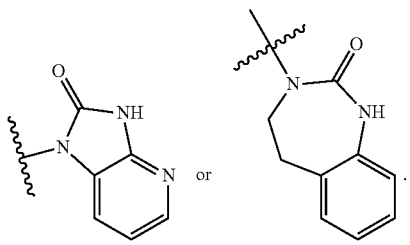 [SMILES: *n1c(=O)[nH]c2ncccc21 ; "or" ; *N1CCc2ccccc2NC1=O ; "."]

Another aspect of the invention is a compound of formula I where $R^5$ is hydrogen, $R^6$ is hydrogen, $R^7$ is hydrogen, $R^8$ is hydrogen, $R^9$ is hydrogen, $R^{10}$ is hydroxy, azido, or amino, and $R^{11}$ is hydrogen; or where $R^5$ is hydrogen, $R^6$ is hydrogen, $R^7$ is hydrogen, $R^8$ is hydrogen, $R^9$ is hydrogen or hydroxy, and $R^{10}$ and $R^{11}$ taken together is oxo; or where $R^5$ is hydrogen, $R^6$ is hydrogen, $R^7$ is hydrogen, $R^8$ is hydrogen, $R^9$ is hydroxy, $R^{10}$ is hydrogen or hydroxy, and $R^{11}$ is hydrogen; or where $R^5$ is hydroxy, $R^6$ is hydrogen, $R^7$ is hydrogen, $R^8$ is hydrogen, $R^9$ is hydrogen, $R^{10}$ is hydrogen, and $R^{11}$ is hydrogen.

Another aspect of the invention is a compound of formula I where $Ar^1$ is phenyl substituted with 2 halo substituents.

Another aspect of the invention is a compound of formula I where $Ar^1$ is 2,3-difluorophenyl.

Another aspect of the invention is a compound of formula I where X is O.

The scope of any instance of a variable, including $R^1$, $R^2$, $R^3$, $R^4$, $R^5$, $R^6$, $R^7$, $R^9$, $R^{10}$, $R^{11}$, $Ar^1$, X, and Y, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons, preferably 1 to 3 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" means fluoro, chloro, bromo, or iodo. "Haloalkyl" and "haloalkoxy" include all halogenated isomers from monohalo substituted alkyl to perhalo substituted alkyl. "Aryl" includes carbocyclic and heterocyclic aromatic ring systems. "Amino" includes primary, secondary, and tertiary amine moieties. "Carbonyl" means CO. "Oxy" means —O—, "Aminocarbonyl" means —N(R)C(=O)—. "Oxycarbonyl" means —OC(=O)—. "Methylenecarbonyl" means —CHC(=O)—. "Amino(cyano)iminomethyl" means —NHC(=NCN)—. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some compounds of the invention may exist in stereoisomeric forms, one example of which is shown below. The invention includes all stereoisomeric and tautomeric forms of the compounds.

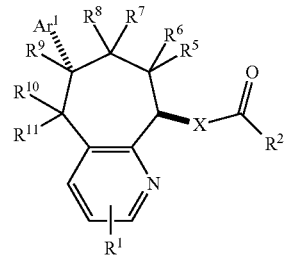

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds may be made by methods known in the art including those described below and including variations within the skill of the art. Some reagents and intermediates are known in the art. Other reagents and intermediates can be made by methods known in the art using readily available materials. The following methods are for illustrative purposes and are not intended to limit the scope of the invention. It will be appreciated by those skilled in the art that there are a number of methods available for the synthesis of these compounds and that their synthesis is not limited to the methods provided in the following examples. Variations of the compounds and the procedures to make them which are not illustrated are within the skill of the art. The variables describing general structural formulas and features in the synthetic schemes are distinct from and should not be confused with the variables in the claims or the rest of the specification. These variables are meant only to illustrate how to make some of the compounds of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Some of the compounds of Formula I can be synthesized through the following general scheme.

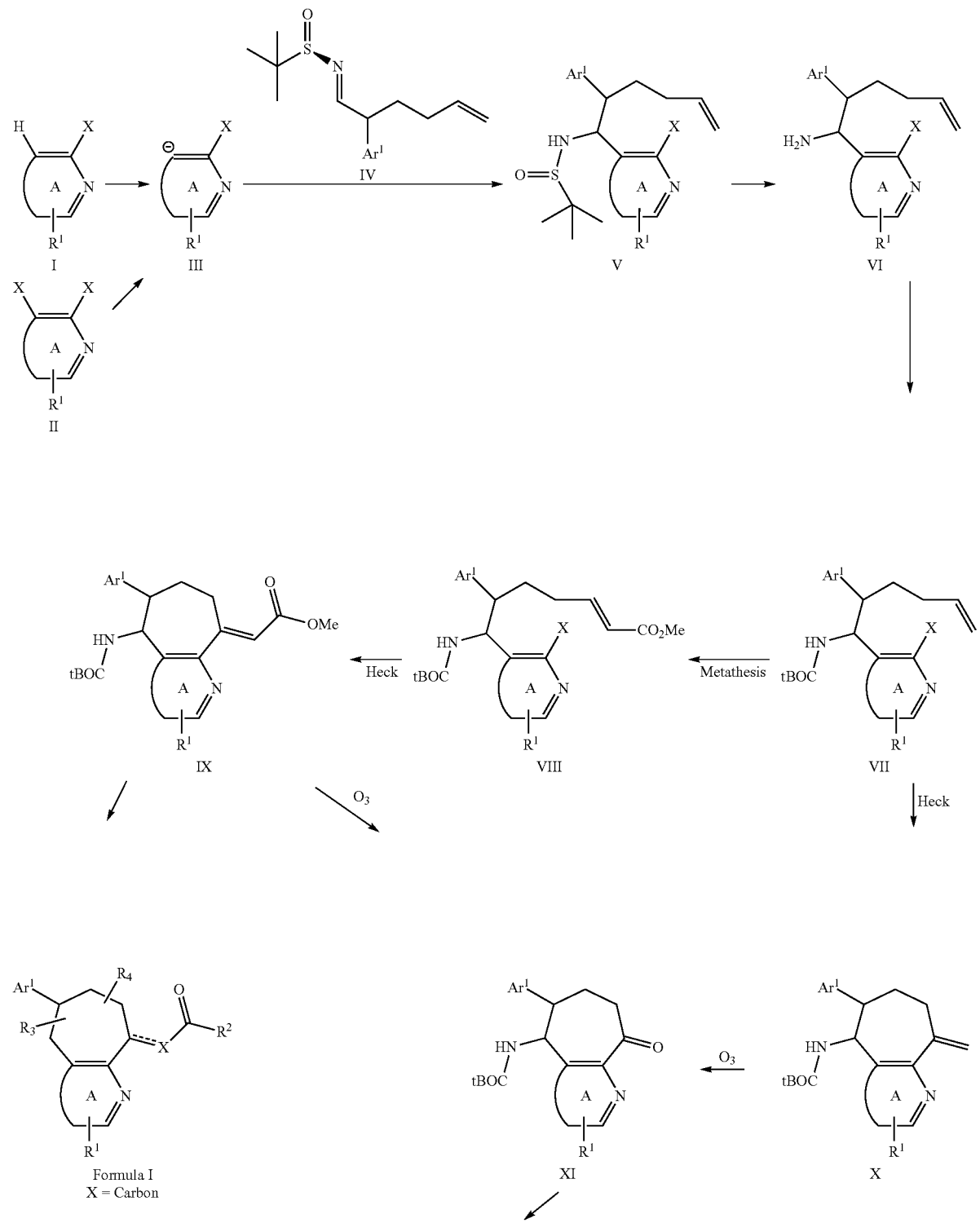

-continued

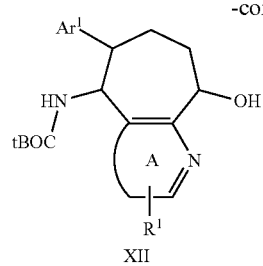
XII

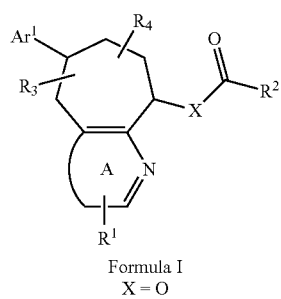
Formula I
X = O

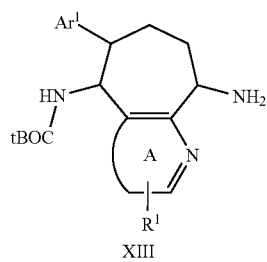
XIII

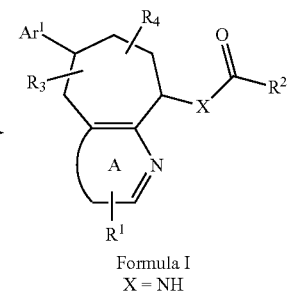
Formula I
X = NH

The anion intermediate III could be generated through either deprotonation of I or halogen-lithium exchange of II, which can react with a key intermediate sulfonamide IV to generate V. The sulfinyl group can be removed by HCl to VI, which can be protected by treatment with t-BOC$_2$O to afford VII. Intermediate VII could undergo intra-molecular Heck reaction to generate X, which after ozonolysis would generate ketone intermediate XI. Alternatively, VII could react with methyl acrylate under known metathesis conditions to afford VIII, which could undergo intra-molecular Heck reaction to afford IX. Intermediate IX could be converted to Formula I through previously known transformations. IX could also be converted to the ketone intermediate XI by ozonolysis. The ketone intermediate can be reduced to the alcohol XII, which by previously known transformations, could be converted either to urea or carbamate analogs of Formula I.

The racemic synthesis of IV can start with phase transfer alkylation of the aryl nitrile compound. The nitrile group could be directly reduced by DIBAL to the aldehyde XV, which could react with t-butylsulfinamide to afford the desired intermediate IV. The synthesis of chiral (R/S) IV can start with XVI, which can be prepared from commercially available pent-4-enal. The chiral aryl group can be introduced by known literature conditions to afford XVII, which under Nef reaction conditions, could be converted to the chiral aldehyde XV. Intermediate XV could react with commercially available (R)-t-butyl-sulfinamide to obtain the chiral intermediate IV.

Synthesis of the Intermediate IV (Racemate and Chiral):

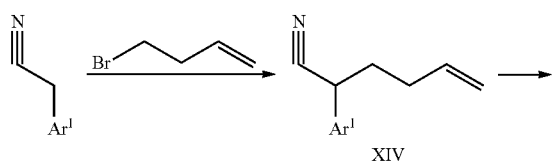

-continued

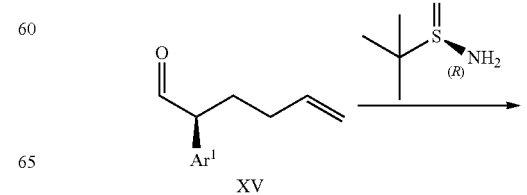

Chiral version:

-continued

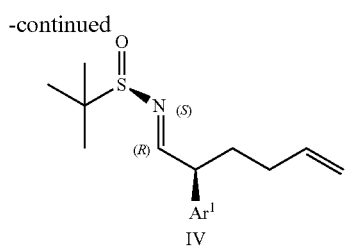

IV

Representative examples are described in the following Schemes.

As shown in Scheme 1, after deprotonation of 2-bromopyrazine with LDA, reaction with intermediate 1 afforded 2 in good yield. Intermediate 2 was converted to 3 by treatment with HCl and then t-butylpyrocarbonate. Under Grubbs' metathesis conditions, 3 reacted with methyl acrylate to generate 4. Under Fu's Heck reaction conditions, 4 was converted to chromatographically separable 5 and 6. Compound 5 was converted to example 1 through intermediate 10. Example 2 was obtained from example 1 by treatment with trifluoroacetic acid. Intermediate 6 was converted to the ketone intermediate 7, which was reduced to the chromatographically separable 8 and 9.

Scheme 1:

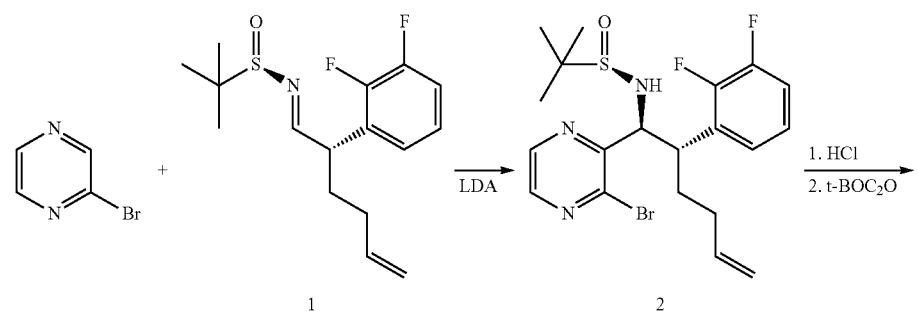

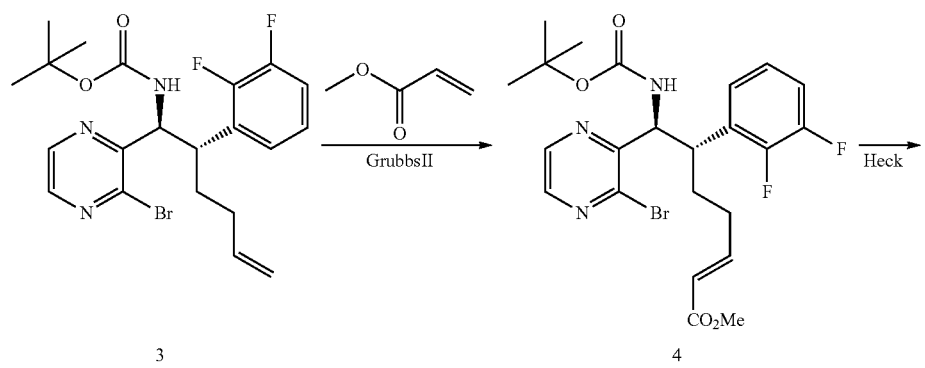

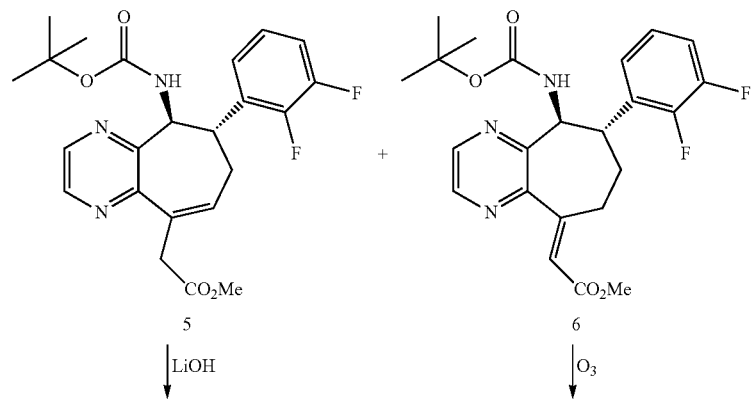

15

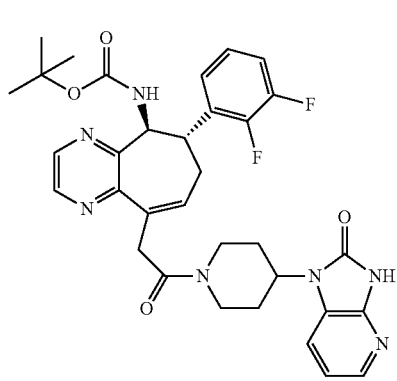

Example 1

↓ TFA

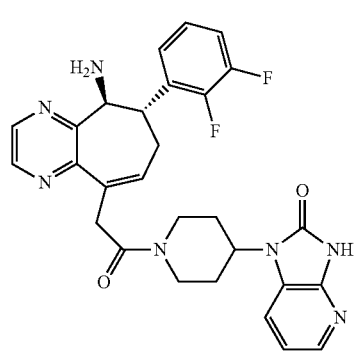

Example 2

-continued

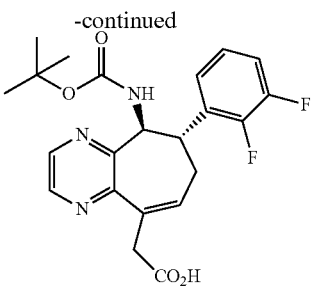

10

16

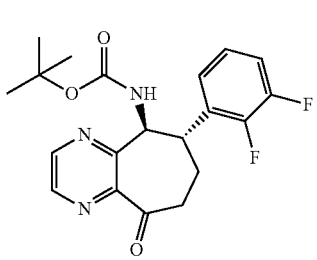

7

NaBH₄ ↙

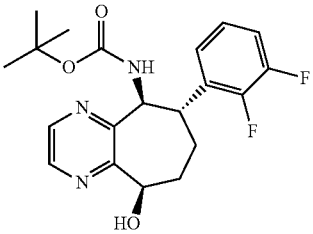 + 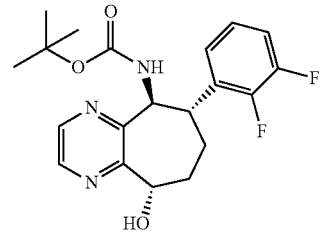

8                9

Alcohol intermediate 8 was converted to example 3 by previously known conditions. Example 4 was obtained by treatment of example 3 with trifluoroacetic acid. Using known reaction conditions, alcohol intermediate 9 was converted to the amine intermediates 12 and 11. Examples 5 and 6 were obtained from 12 by known reaction conditions. Treatment of either example 5 or 6 afforded example 7.

Scheme 2:

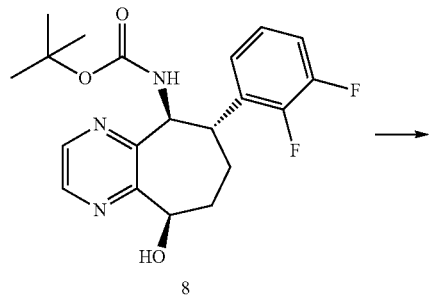

8

-continued

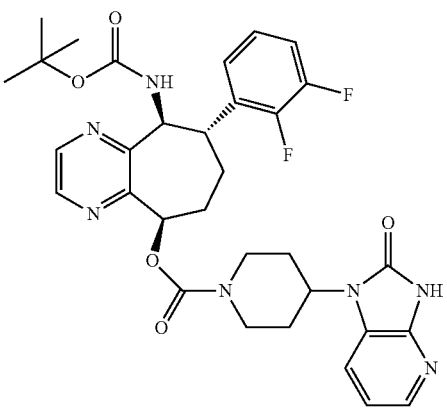

Example 3

17
-continued

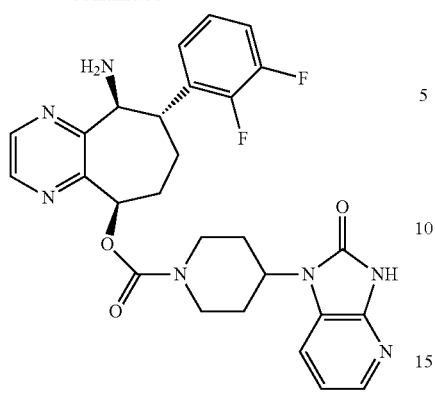

Example 4

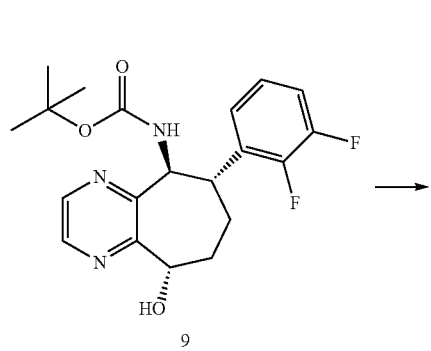
9

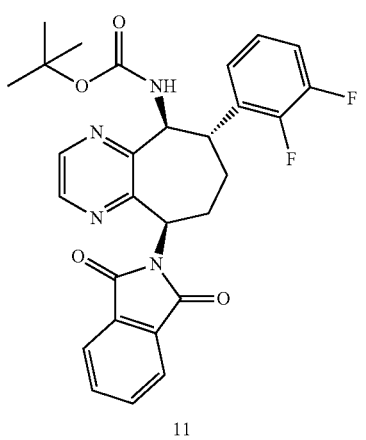
11

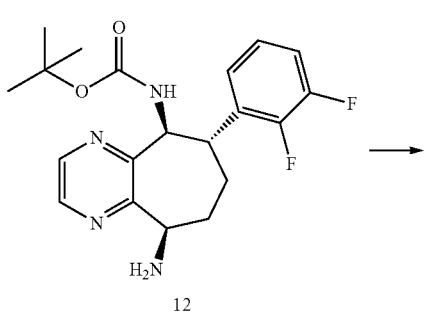
12

18
-continued

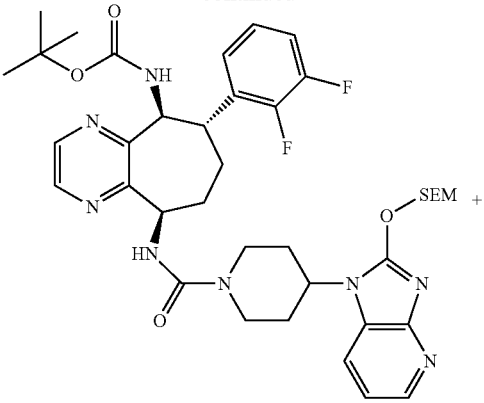

Example 5

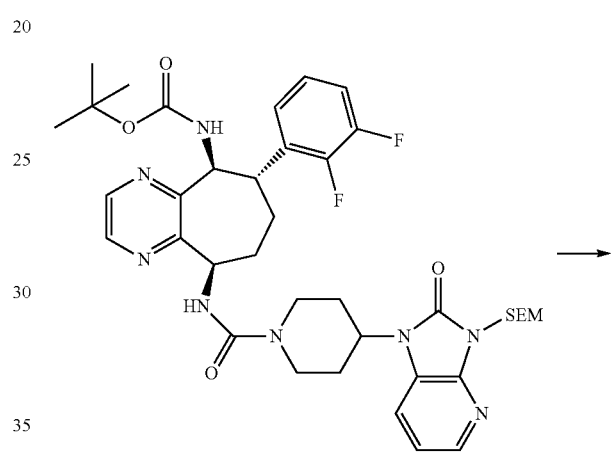

Example 6

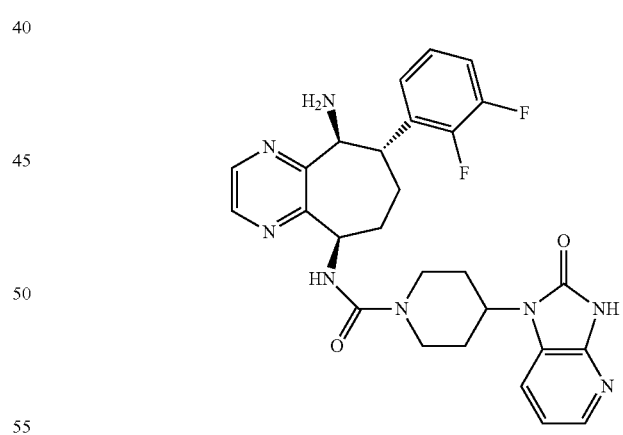

Example 7

As shown in Scheme 3, after deprotonation of 2,4-dibromo-thiazole with LDA and reaction with intermediate 1, one equivalent of n-BuLi was able to remove the 2-bromo substituent to afford intermediate 13. Compound 13 was converted to 14 and then to 15 under conditions already described. Also following previous conditions, compound 15 was converted to 16 and then the ketone intermediate 17, which was reduced to alcohol intermediate alcohol 18. Intermediate 18 was converted to example 8, through intermediates 19, following previously described reaction conditions.

Scheme 3:

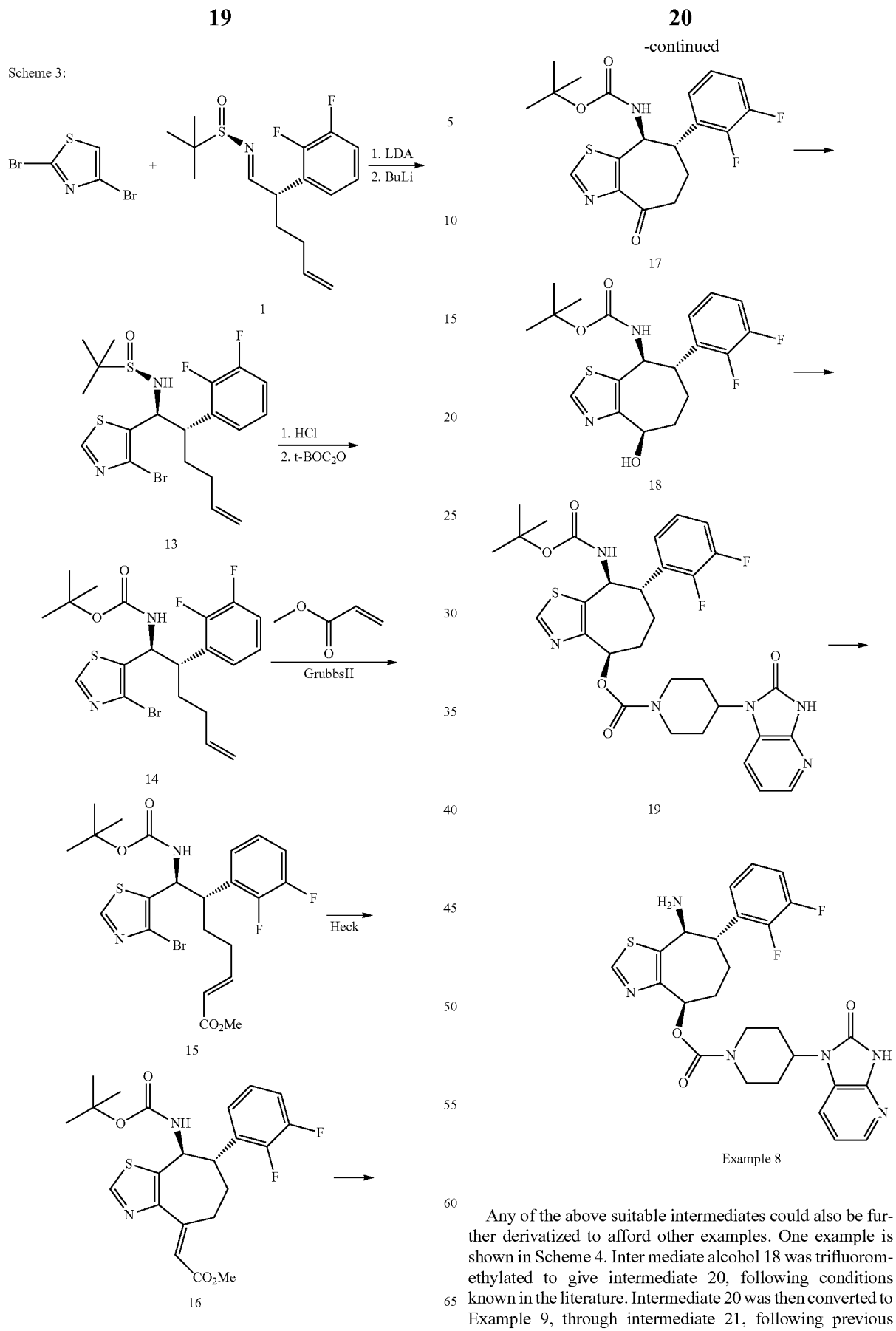

Any of the above suitable intermediates could also be further derivatized to afford other examples. One example is shown in Scheme 4. Intermediate alcohol 18 was trifluoromethylated to give intermediate 20, following conditions known in the literature. Intermediate 20 was then converted to Example 9, through intermediate 21, following previous described conditions.

Scheme 4:

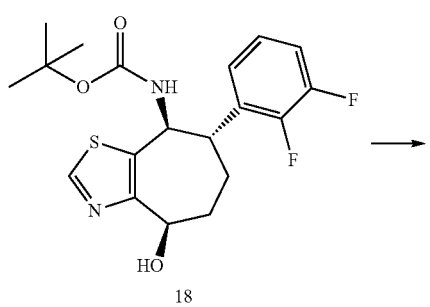

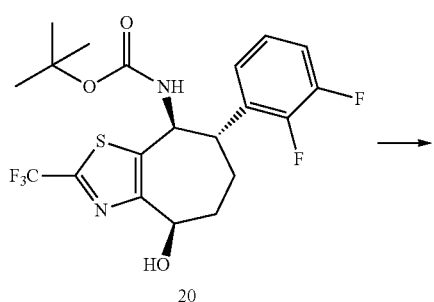

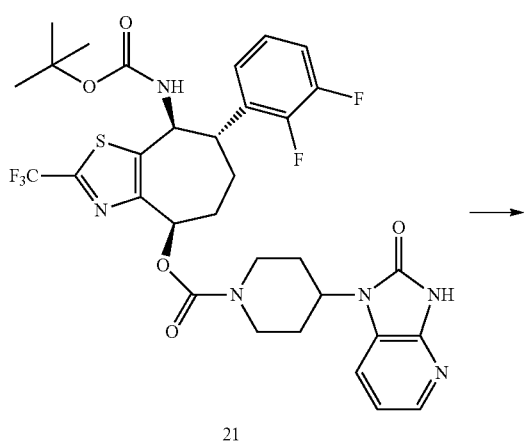

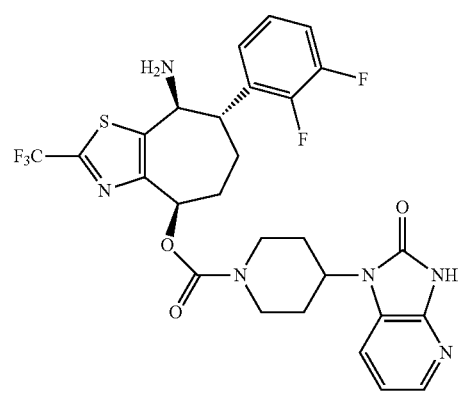

Example 9

TABLE 1

| | Human CGRP Binding | |
|---|---|---|
| Example | | Human CGRP Receptor IC$_{50}$ (nM) |
| 1 | | 570 |
| 2 | | 470 |
| 3 | | 1.1 |
| 4 | | 0.11 |
| 5 | | 74 |
| 6 | | 910 |
| 7 | | 1.1 |
| 8 | | 0.095 |
| 9 | | 0.130 |

EXPERIMENTAL SECTION

Synthesis of Intermediate 1

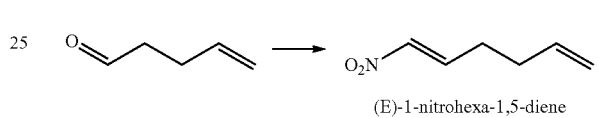

(E)-1-nitrohexa-1,5-diene (E)-1-nitrohexa-1,5-diene

In an oven-dried 1 L round-bottomed flask pent-4-enal (11.3 g, 134 mmol) was dissolved in toluene (300 mL) to give a colorless solution. After cooling to 0° C., nitromethane (72.4 mL, 1343 mmol) and 1,1,3,3-tetramethylguanidine (1.685 mL, 13.43 mmol) were added. After the mixture was stirred at 0° C. for 60 min, TLC showed a major product (4:1 hexane/ethyl acetate). Methanesulfonyl chloride (15.7 mL, 202 mmol) and triethylamine (28 mL, 202 mmol) were added. The cooling bath was removed and the mixture was stirred at r.t. for 1 h. After 1 h, a further 0.5 equiv. of methanesulfonyl chloride (5.2 mL) and triethylamine (9.3 mL) were added to the mixture and the reaction continued for another h. It was quenched with saturated sodium bicarbonate solution and diluted with diethyl ether. The layers were separated and the aqueous layer was extracted with diethyl ether. The combined organic layers were washed with brine, dried with sodium sulfate, and concentrated under high vacuum to give a tan oil. The residue was purified by flash column chromatography up to 20% ethyl acetate/hexanes. The major uv-active fraction was pooled and concentrated to a light yellow oil (further dried under house vac over 3 days: 12.30 g, 72%): $^1$H NMR (4.00 MHz, CHLOROFORM-d) δ ppm 7.24 (ddd, J=13.74, 7.15, 6.96 Hz, 1H) 6.98 (d, J=13.55 Hz, 1H) 5.67-5.86 (m, 1H) 4.98-5.14 (m, 2H) 2.37 (q, J=7.03 Hz, 2H) 2.27 (q, J=6.94 Hz, 2H); $^{13}$C NMR (101 MHz, CHLOROFORM-d) δ ppm 140.82-141.82 (m, 1C) 139.50 (d, J=10.02 Hz, 1C) 135.60 (d, J=10.02 Hz, 1C) 115.56-116.67 (m, 1C) 30.49-31.82 (m, 1C) 26.73-27.94 (m, 1C).

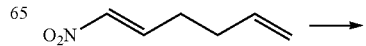

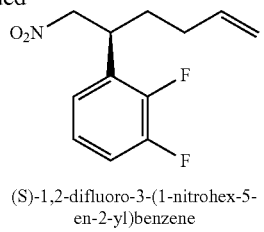

(S)-1,2-difluoro-3-(1-nitrohex-5-
en-2-yl)benzene

(S)-1,2-Difluoro-3-(1-nitrohex-5-en-2-yl)benzene

In a 1 L round-bottom flask was dissolved (E)-1-nitrohexa-1,5-diene (12.30 g, 97 mmol) and 2,3-difluorophenylboronic acid (38.2 g, 242 mmol) in dioxane (315 mL) to give a colorless suspension. Water (6.1 mL, 340 mmol) was added. The mixture was degassed with nitrogen and in a sonicator for 20 min. Sodium bicarbonate (4.06 g, 48.4 mmol) and (S)-(+ 2,2'-bis(diphenylphosphino)-1,1'-binaphthyl (1.807 g, 2.90 mmol) and acetylacetonatobis(ethylene)rhodium (I) (0.749 g, 2.90 mmol) were added to the solution under nitrogen. The mixture was stirred at rt for 2 min, and then heated to 35° C. for 6 h under nitrogen. Reaction was continued for another 8 h at 35° C.

The mixture was diluted with ethyl acetate and water. The layers were separated and the aqueous layer was extracted with ethyl acetate. The combined organic layers were washed with brine, dried with sodium sulfate, and concentrated to a tan oil. Flash column chromatography up to 15% ethyl acetate/hexane afforded a major fraction which was pooled and concentrated to the product as a colorless oil (22.38 g, 96%): $^1$H NMR (400 MHz, CHLOROFORM-d) δ ppm 7.03-7.17 (m, 2H) 6.91-7.02 (m, 1H) 5.75 (dddd, J=16.81, 10.42, 6.53, 6.40 Hz, 1H) 4.94-5.05 (m, 2H) 4.67 (dd, J=7.53, 2.26 Hz, 2H) 3.81 (t, J=7.28 Hz, 1H) 1.94-2.08 (m, 2H) 1.77-1.94 (m, 2H); $^{13}$C NMR (101 MHz, CHLOROFORM-d) δ ppm 151.74-149.14 (dd, J=13.13 and 249.47 Hz, 1C) 150.15-147.55 (dd, J=13.13 and 249.47 Hz, 1C) 136.32 (d, J=10.02 Hz, 1C) 128.18 (d, J=10.79 Hz, 1C) 124.15 (br. s., 1C) 123.68 (d, J=3.85 Hz, 1C) 115.82-117.00 (m, 1C) 115.54 (br. s., 1C) 78.49 (br. s., 1C) 37.85 (d, J=11.56 Hz, 1C) 30.63 (s, 1C) 30.54 (s, 1C); $^{19}$F NMR (376 MHz, CHLOROFORM-d) δ ppm −137.24 (br. s., 1F) −142.38 (br. s., 1F).

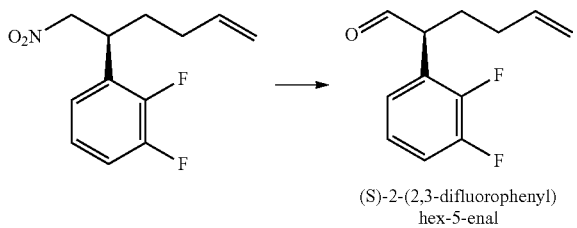 [SMILES: C=CCC[C@H](C[N+](=O)[O-])c1cccc(F)c1F ; C=CCC[C@H](C=O)c1cccc(F)c1F]

(S)-2-(2,3-difluorophenyl)
hex-5-enal

(S)-2-(2,3-Difluorophenyl)hex-5-enal

In a 250 mL round-bottomed flask was dissolved (S)-1,2-difluoro-3-(1-nitrohex-5-en-2-yl)-benzene (4.14 g, 17.2 mmol) in methanol (21 mL) under nitrogen. After cooling to 0° C., sodium methoxide (4.12 mL, 18.0 mmol) was added via syringe. After stirring at 0° C. for 30 min, the temperature was lowered to −60° C. Conc. sulfuric acid (2.93 mL, 54.9 mmol) in 21 mL methanol was added dropwise. The resulting milky mixture was stirred at −60 to −20° C. for 4 h. It was diluted with ethyl acetate and saturated ammonium chloride solution. The layers were separated. The aqueous layer was extracted with ethyl acetate (2×40 mL). The combined organic layers were washed with brine, dried, and concentrated to a give tan oil (4.8 g), which was dissolved in chloroform (124 mL) Water (31 mL) was added followed by slow addition of trifluoroacetic acid (31 mL). The mixture was stirred at rt overnight for 18 h. The layers were separated. The aqueous layer was extracted with methylene chloride. The combined organic layers were dried and concentrated to give a light yellow oil (5 g, 100%). This was directly carried onto next reaction immediately.

Intermediates 1

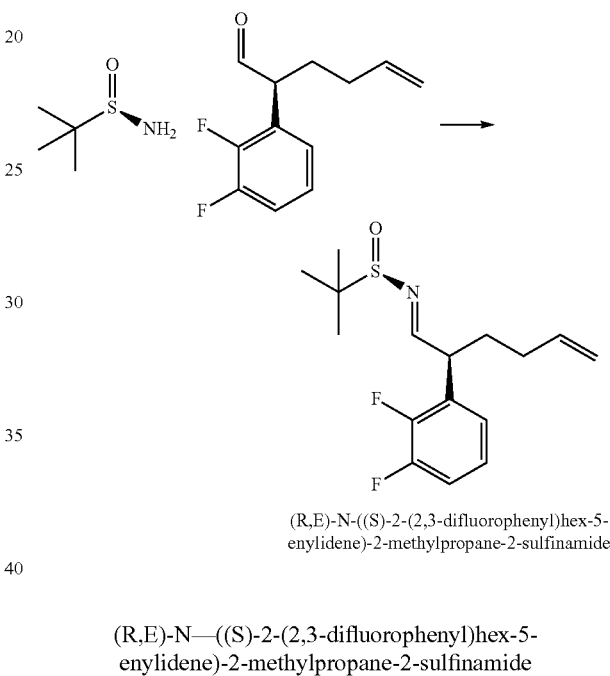

(R,E)-N-((S)-2-(2,3-difluorophenyl)hex-5-
enylidene)-2-methylpropane-2-sulfinamide

(R,E)-N—((S)-2-(2,3-difluorophenyl)hex-5-enylidene)-2-methylpropane-2-sulfinamide In a 500 mL round-bottomed flask was dissolved (S)-2-(2, 3-difluorophenyl)hex-5-enal (3.61 g, 17.2 mmol) (freshly azeotroped with dry benzene) and (R)-2-methylpropane-2-sulfinamide (2.08 g, 17.2 mmol) in tetrahydrofuran (100 mL) to give a yellow solution. Titanium(IV) ethoxide (36.0 mL, 34.3 mmol) was added dropwise, and the mixture was stirred at rt under nitrogen for 6 h. It was transferred to a stirred solution of brine (90 mL) and a white solid was formed. This was filtered through a plug of celite and washed with ethyl acetate. The eluent was concentrated to give a tan oil. The residue was purified by flash column chromatography up to 40% ethyl acetate/hexane afforded the desired product (3.94 g, 73% for 2 steps) as a light yellow oil: $^1$H NMR (400 MHz, CHLOROFORM-d) δ ppm 8.09 (d, J=4.52 Hz, 1H) 7.02-7.14 (m, 2H) 6.97 (d, J=8.28 Hz, 1H) 5.68-5.87 (m, 1H) 5.02 (d, J=13.05 Hz, 2H) 4.07-4.18 (m, 1H) 2.19 (dt, J=13.30, 6.65 Hz, 1H) 2.05-2.13 (m, 2H) 1.90-2.03 (m, 1H) 1.17 (s, 9H); $^{19}$F NMR (376 MHz, CHLOROFORM-d) δ ppm −137.55 (br. s., 1F) −142.03 (br. s., 1F); $^{13}$C NMR (101 MHz, CHLOROFORM-d) δ ppm 167.97 (s, 1C) 151.70-149.09 (m, 1C) 149.93-147.27 (m, 1C) 136.71 (d, J=9.25 Hz, 1C) 128.43 (d, J=9.25 Hz, I C) 122.99-124.42 (m, 1C) 115.88-115.68 (m, 1C) 115.37 (m, 1C) 109.63 (s, 1C) 56.77 (s, 1C) 43.94 (d, J=12.33 Hz, 1C) 30.83 (s, 1C) 30.40 (s, 1C) 21.96 (d, J=5.39 Hz, 3C).

Intermediates 2

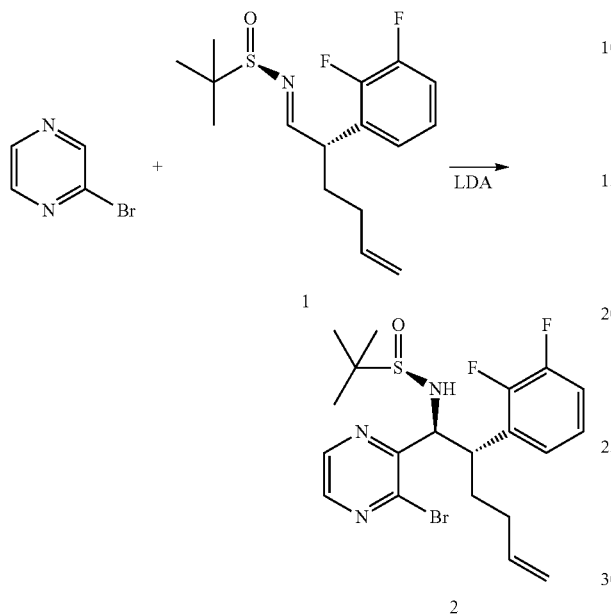

(R)—N-((1S,2S)-1-(3-bromopyrazin-2-yl)-2-(2,3-difluorophenyl)hex-5-enyl)-2-methylpropane-2-sulfinamide In an oven-dried 250 mL round-bottomed flask was dissolved diisopropylamine (1.7 mL, 12 mmol) in tetrahydrofuran (40 mL) to give a colorless solution under nitrogen. After cooling to −30° C., n-BuLi (4.3 mL, 11 mmol) was added, and the mixture was briefly warmed up to rt for 3 min. After cooling down to −78° C., 2-bromopyrazine (0.98 mL, 10.7 mmol) was added dropwise via syringe. The resulting yellow solution was stirred at −78° C. for 5 min. (R,E)-N—((S)-2-(2,3-difluorophenyl)hex-5-enylidene)-2-methylpropane-2-sulfinamide (2.089 g, 6.67 mmol) in 4 mL anhydrous tetrahydrofuran (plus 3 mL rinse) was added via canuula, and the mixture was stirred for 2 h at −75° C. The reaction was quenched with saturated sodium bicarbonate solution and diluted with ethyl acetate. The layers were separated. The aqueous layer was extracted with ethyl acetate. The combined organic layers were washed with brine, dried, and concentrated to give a tan oil. Flash column chromatography up to 80% ethyl acetate/hexane afforded the desired product (1.964 g, 62%) as a dense tan oil: $^1$H NMR (400 MHz, CHLOROFORM-d) δ ppm 8.33 (d, J=2.26 Hz, 1H) 8.26 (d, J=2.26 Hz, 1H) 6.99-7.22 (m, 3H) 5.74 (d, J=6.53 Hz, 1H) 5.18 (dd, J=9.29, 5.27 Hz, 1H) 4.85-4.99 (m, 2H) 4.30 (d, J=9.54 Hz, 1H) 3.66-3.77 (m, 1H) 2.17 (br. s., 1H) 1.80-2.04 (m, 3H) 1.05 (s, 9H); $^{19}$F NMR (376 MHz, CHLOROFORM-d) δ ppm −138.41 (d, J=15.61 Hz, 1F) −144.20--143.20 (m, 1F); $^{13}$C NMR (101 MHz, CHLOROFORM-d) δ ppm 155.19 (s, 1C) 151.32-149.72 (dd, J=13.87 and 249.47 Hz, 1C) 150.24-147.67 (dd, J=12.72 and 246.95 Hz, 1C) 142.89 (s, 1C) 141.44 (br. s., 1C) 140.47 (s, 1C) 136.93 (d, J=10.02 Hz, 1C) 127.54 (d, J=10.79 Hz, 1C) 124.12-124.96 (m, 1C) 123.41-123.97 (m, 1C) 115.23-115.83 (m, 1C) 115.09 (s, 1C) 59.93-60.56 (m, 1C) 56.10-56.69 (m, 1C) 40.72-41.81 (m, 1C) 30.81 (s, 1C) 30.34 (br. s., 1C) 21.94 (q, J=6.17 Hz, 3C).

Intermediate 3

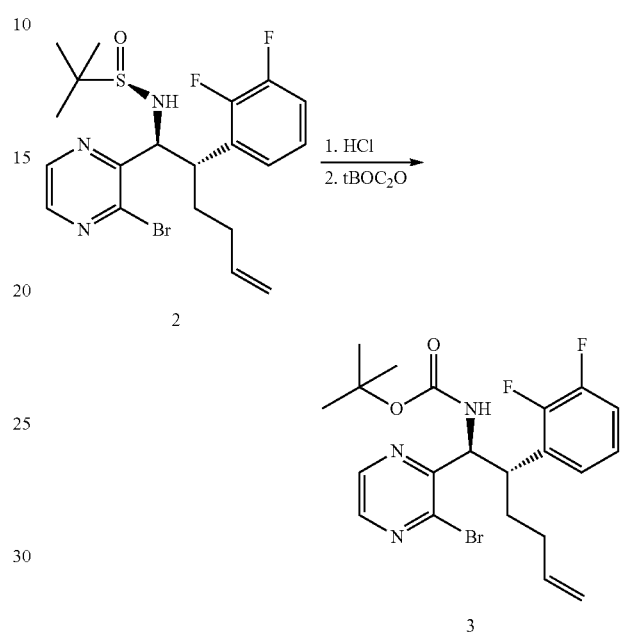

tert-Butyl (1S,2S)-1-(3-bromopyrazin-2-yl)-2-(2,3-difluorophenyl)hex-5-enylcarbamate In a 250 mL round-bottomed flask was (R)—N-((1S)-1-(3-bromopyrazin-2-yl)-2-(2,3-difluorophenyl)hex-5-enyl)-2-methylpropane-2-sulfinamide (1.96 g, 4.16 mmol) in methanol (17 mL) to give a tan solution. HCl (4M in dioxane, 4.2 mL, 17 mmol) was added, and the mixture was stirred at rt for 1 h. Volatiles were removed in vacuo and the tan residue was diluted with ether and concentrated. The remaining tan foam was directly used in the next reaction. In the same round-bottomed flask was dissolved (1S,2S)-1-(3-bromopyrazin-2-yl)-2-(2,3-difluorophenyl)hex-5-en-1-amine (1.532 g, 4.16 mmol) (crude HCl salt) and t-butylpyrocarbonate (1.449 mL, 6.24 mmol) in methylene chloride (22 mL) to give a tan solution. triethylamine (1.28 mL, 9.15 mmol) was added dropwise, and the mixture was stirred at rt for 2 h. LCMS showed complete conversion. It was concentrated to dryness, and directly subject to flash column chromatography up to 40% ethyl acetate/hexane to afford the desired product (1.80 g, 92% for 2 steps) as colorless oil: $^1$H NMR (400 MHz, CHLOROFORM-d) δ ppm 8.27 (d, J=17.07 Hz, 2H) 6.92-7.14 (m, 3H) 5.69 (dd, J=10.29, 5.77 Hz, 1H) 5.63 (dd, J=9.41, 5.90 Hz, 1H) 5.41 (d, J=9.54 Hz, 1H) 4.84-4.95 (m, 2H) 3.65 (br. s., 1H) 1.88-2.08 (m, 3H) 1.81 (br. s., 1H) 1.30-1.41 (m, 9H). A slightly more polar diastereomer (generally <10% if there was minimum epimerization at the aldehyde stage) could be removed at this stage: $^1$H NMR (400 MHz, CHLOROFORM-d) δ ppm 8.46 (d, J=2.26 Hz, 1H) 8.20 (d, J=2.51 Hz, 1H) 6.88-7.11 (m, 3H) 5.66-5.81 (m, 1H)

5.60 (t, J=8.91 Hz, 1H) 5.51 (d, J=9.29 Hz, 1H) 4.83-5.00 (m, 2H) 3.55 (d, Hz, 1H) 1.87-2.06 (m, 3H) 1.73-1.86 (m, 1H) 1.44 (s, 9H).

Intermediate 4

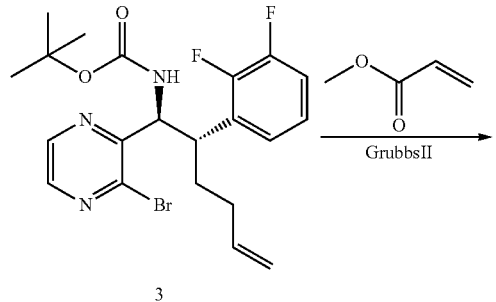

3

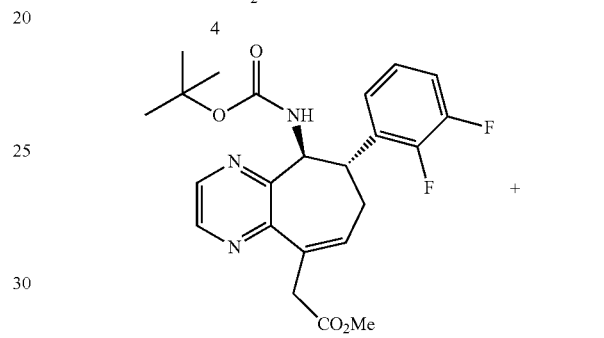

4

(6S,7S,E)-Methyl 7-(3-bromopyrazin-2-yl)-7-(tert-butoxycarbonylamino)-6-(2,3-difluorophenyl)hept-2-enoate In a 250 mL round-bottomed flask was dissolved tert-butyl (1S,2S)-1-(3-bromopyrazin-2-yl)-2-(2,3-difluorophenyl) hex-5-enylcarbamate (354.6 mg, 0.757 mmol) in methylene chloride (16 mL) to give a colorless solution. Methyl acrylate (0.21 mL, 2.3 mmol) and Grubbs-If catalyst (32.1 mg, 0.038 mmol) were added, and the mixture was stirred under reflux for 3 h under nitrogen. TLC showed complete conversion. Volatile components were removed in vacuo and the residue was purified by flash column chromatography upto 50% ethyl acetate/hexane to afford the desired product (335 mg, 84%) as a colorless oil: $^1$H NMR (400 MHz, CHLOROFORM-d) δ ppm 8.31 (s, 1H) 8.28 (s, 1H) 6.98-7.14 (m, 3H) 6.80-6.94 (m, 1H) 5.76 (d, J=16.56 Hz, 1H) 5.59-5.71 (m, 1H) 5.42 (d, 0.1-9.54 Hz, 1H) 3.71 (s, 3H) 3.59-3.69 (m, 1H) 2.09-2.29 (m, 2H) 1.96-2.04 (m, 1H) 1.83-1.95 (m, 1H) 1.37 (s, 9H).

Intermediates 5 and 6

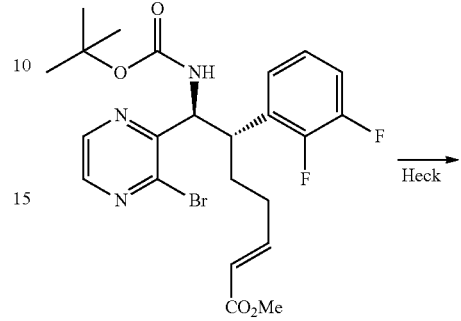

4

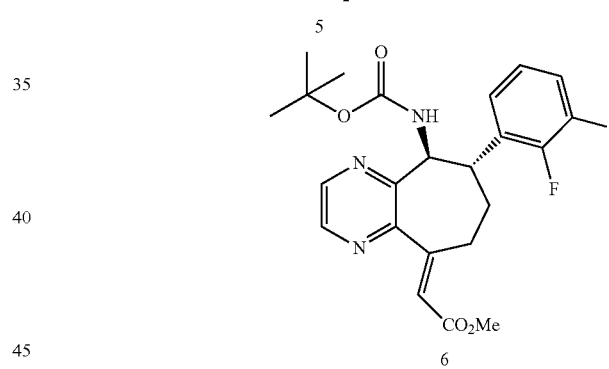

5

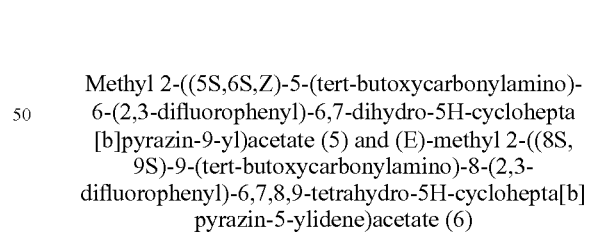

6

Methyl 2-((5S,6S,Z)-5-(tert-butoxycarbonylamino)-6-(2,3-difluorophenyl)-6,7-dihydro-5H-cyclohepta[b]pyrazin-9-yl)acetate (5) and (E)-methyl 2-((8S,9S)-9-(tert-butoxycarbonylamino)-8-(2,3-difluorophenyl)-6,7,8,9-tetrahydro-5H-cyclohepta[b]pyrazin-5-ylidene)acetate (6)

In a 25 mL microwave tube was dissolved (6S,7S,E)-methyl 7-(3-bromopyrazin-2-yl)-7-(tert-butoxycarbonylamino)-6-(2,3-difluorophenyl)hept-2-enoate (335 mg, 0.636 mmol), and bis(tri-t-butylphosphine)palladium (16.3 mg, 0.032 mmol) in dioxane (14 mL) (degassed)) to give a yellow solution under nitrogen. Methyl dicyclohexylamine (0.15 mL, 0.70 mmol) was added, and the reaction was sealed under nitrogen, The mixture was stirred at rt for 1 min then at 160° C. under microwave irradiation for 2 h. TLC (1/1 ethyl acetate/hexane) showed little starting material and mainly the desired isomer. The mixture was partitioned between water and ethyl acetate. The layers were separated. The aqueous layer was extracted with ethyl acetate twice. The combined organic layers were washed with brine, dried with sodium sulfate, and concentrated. The residue was purified by flash column chromatography up to 70% ethyl acetate to afford the cyclized product 6 (153 mg, 54%) as a white solid, as well as the isomer (5, 69.5 mg, 24.5%) as a colorless oil. 6: $^1$H NMR (400 MHz, CDCl$_3$) δ 8.55-8.52 (m, 2H), 7.35 (d, J=8.2 Hz, 1H), 7.13-7.06 (m, 2H), 6.49 (s, 1H), 5.70 (d, J=9.5 Hz, 1H), 5.40-5.30 (m, 1H), 3.79 (s, 3H), 3.51-3.37 (m, 2H), 3.09 (dd, J=19.1, 6.7 Hz, 1H), 2.05 (s, 1H), 1.95-1.80 (m, 1H), 1.29 (s, 9H). 5: $^1$H NMR (400 MHz, CDCl$_3$) δ 8.51 (d, J=2.4 Hz, 1H), 8.42 (d, J=2.4 Hz, 1H), 7.39 (d, J=7.6 Hz, 1H), 7.13-7.03 (m, 2H), 6.51 (t, J=6.8 Hz, 1H), 5.87 (d, J=9.4 Hz, 1H), 5.42 (t, J=9.7 Hz, 1H), 3.95-3.76 (m, 2H), 3.69 (s, 3H), 3.65-3.54 (m, 1H), 2.42 (t, J=5.8 Hz, 2H), 1.28 (d, J=5.3 Hz, 9H).

Intermediate 7

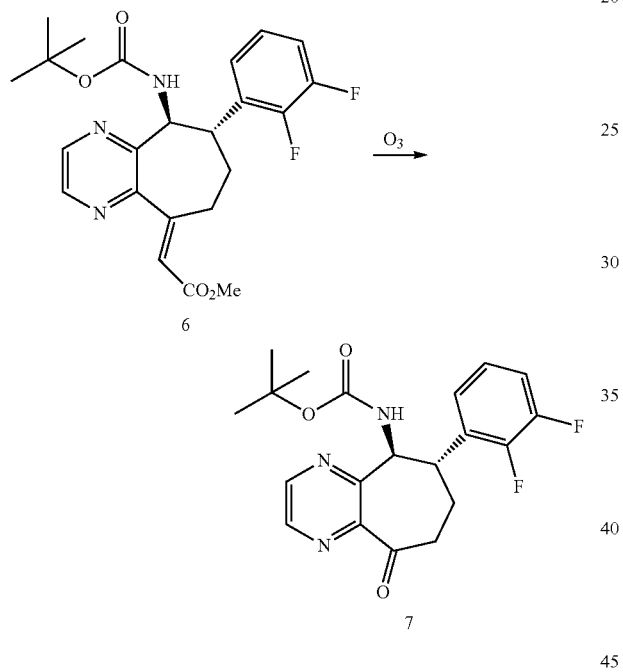

tert-Butyl (5S,6S)-6-(2,3-difluorophenyl)-9-oxo-6,7,8,9-tetrahydro-5H-cyclohepta[b]pyrazin-5-ylcarbamate In a 250 mL round-bottomed flask was dissolved (E)-methyl 2-((8S,9S)-9-(tert-butoxycarbonylamino)-8-(2,3-difluorophenyl)-6,7,8,9-tetrahydro-5H-cyclohepta[b]pyrazin-5-ylidene)acetate (153 mg, 0.343 mmol) in methylene chloride (50 mL) to give a colorless solution. After cooling to −78° C., ozone was bubbled through the solution for 5 min. TLC (1/1 ethyl acetate/hexane) showed a new more polar peak. Nitrogen was then bubbled through the solution for 5 min, and a few drops of dimethylsulfide were added. Volatiles were removed in vacuo. The residue was directly purified by flash column chromatography up to 60% ethyl acetate/hexane to afford the desired product (88 mg, 66%) as a colorless oil: $^1$H NMR (400 MHz, CDCl$_3$) δ 8.71 (d, J=2.3 Hz, 1H), 8.69 (d, J=2.4 Hz, 1H), 7.28 (s, 1H), 7.13-7.06 (m, 2H), 5.76 (d, J=9.0 Hz, 1H), 5.61-5.46 (m, J=7.5 Hz, 1H), 3.58-3.44 (m, 1H), 3.18-3.03 (m, 1H), 2.88 (did, =17.1, 3.3 Hz, 1H), 2.18-2.10 (m, J=5.0 Hz, 2H), 1.26 (s, 9H); $^{19}$F NMR (376 MHz, CDCl3) δ −137.90 (d, J=17.8 Hz), −142.15 (d, J=16.9 Hz); $^{13}$C NMR (101 MHz, CDCl3) δ 201.00 (s), 154.80 (s), 152.87 (s), 150.69 (dd, J=174.1, 13.3 Hz), 148.30 (dd, J=160.0, 12.4 Hz), 147.27 (s), 145.56-145.00 (m), 143.97 (d, J=6.7 Hz), 130.66 (d, J=10.8 Hz), 123.74 (s), 122.57 (s), 115.67 (s), 79.73 (s), 52.93 (s), 39.58 (s), 36.88 (s), 28.61-26.78 (m), 26.11 (s).

Intermediates 8 and 9

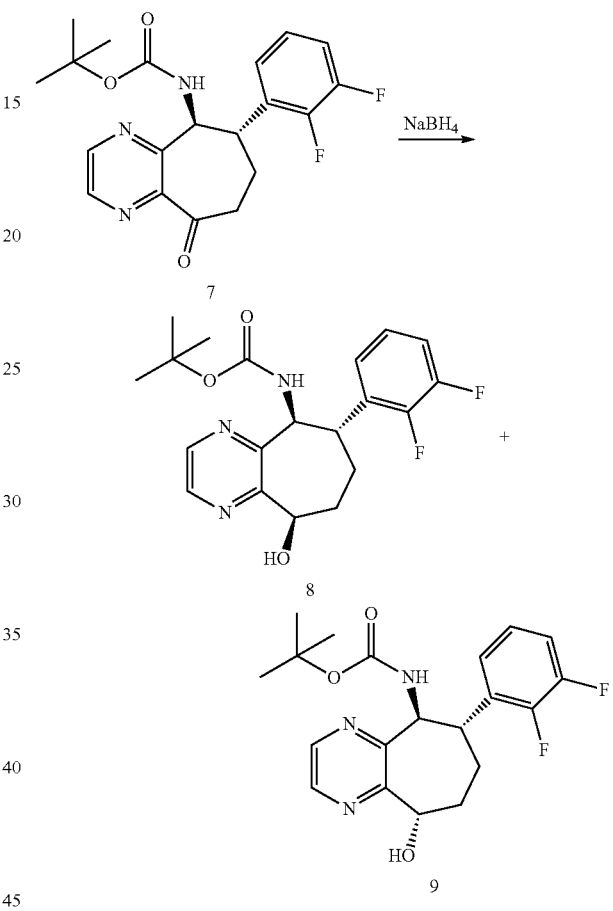

tert-Butyl (5S,6S,9R)-6-(2,3-difluorophenyl)-9-hydroxy-6,7,8,9-tetrahydro-5H-cyclohepta[b]pyrazin-5-ylcarbamate (8) and tert-butyl (5S,6S,9S)-6-(2,3-difluorophenyl)-9-hydroxy-6,7,8,9-tetrahydro-5H-cyclohepta[b]pyrazin-5-ylcarbamate (9)

In a 100 mL round-bottomed flask was dissolved tert-butyl (5S,6S)-6-(2,3-difluorophenyl)-9-oxo-6,7,8,9-tetrahydro-5H-cyclohepta[b]pyrazin-5-ylcarbamate (88 mg, 0.23 mmol) in methanol (4 mL) to give a colorless solution. Sodium borohydride (25.6 mg, 0.678 mmol) was added, and the mixture was stirred at it for 2 h, methanol was removed in vacuo and the residue was partitioned between water and ethyl acetate. The layer was separated. The organic layer was washed with brine, dried with sodium sulfate and concentrated. The residue was purified by flash column chromatography up to 70% ethyl acetate/hexane to afford the less polar product (8, 41 mg, 46%) as a white solid and the more polar product (9, 35 mg, 40%) as a colorless oil. 8: $^1$H NMR (400 MHz, CDCl$_3$) δ 8.52 (d, J=2.5 Hz, 1H), 8.47 (d, J=2.6 Hz, 1H), 7.24 (dd, J=7.7, 5.0 Hz, 1H), 7.11-6.98 (m, 2H), 6.19 (d, J=9.1 Hz, 1H), 5.23 (d, J=4.2 Hz, 1H), 5.16 (t, J=9.6 Hz, 1H), 5.12-5.06 (m, 1H), 3.02 (t, J=10.9 Hz, 1H), 2.55 (td, J=14.7, 2.9 Hz, 1H), 2.48-2.38 (m, 1H), 2.24-2.14 (m, 1H), 1.54 (ddd, J=16.0, 14.1, 3.0 Hz, 1H), 1.22 (s, 9H); $^{19}$F NMR (376 MHz, CDCl$_3$) δ −139.00−−139.52 (m), −142.39 (s); $^{13}$C NMR (101 MHz, CDCl3) δ 154.66 (s), 154.40 (s), 152.82 (s), 150.22 (dd, J=163.2, 13.4 Hz), 147.77 (dd, J=160.1, 13.2 Hz), 141.41 (s), 140.15 (s), 131.55 (s), 131.44 (s), 123.32 (d, J=15.1 Hz), 114.84 (d, J=17.1 Hz), 79.10 (s), 70.18 (s), 55.40 (s), 41.19 (s), 35.54 (s), 32.54 (s), 27.71 (d, J=4.6 Hz). 9: $^1$H NMR (400 MHz, CDCl$_3$) δ 8.40 (d, J=2.5 Hz, 1H), 8.32 (d, J=2.5 Hz, 1H), 7.31 (s, 1H), 7.04 (dt, J=7.4, 5.8 Hz, 2H), 5.97 (d, J=9.3 Hz, 1H), 5.89 (t, J=9.6 Hz, 1H), 5.17 (d, J=6.8 Hz, 1H), 4.08 (s, 1H), 3.16 (t, J=9.7 Hz, 1H), 2.91 (dd, J=23.6, 11.5 Hz, 1H), 2.40-2.28 (m, 1H), 1.99-1.88 (m, 1H), 1.81 (t, J=13.3 Hz, 1H), 1.24 (d, J=5.9 Hz, 9H); $^{19}$F NMR (376 MHz, CDCl$_3$) δ −139.45 (d, J=20.1 Hz), −143.03 (s); $^{13}$C NMR (101 MHz, CDCl3) δ 155.16 (s), 154.85 (s), 154.66 (s), 150.17 (dd, J=171.9, 13.1 Hz), 147.73 (dd, J=170.2, 14.0 Hz), 141.71 (s), 140.81 (s), 132.49 (s), 132.38 (s), 123.41 (d, J=35.2 Hz), 114.50 (s), 78.94 (s), 74.08 (s), 54.72 (s); 41.38 (s), 31.15 (s), 28.72 (s), 27.77 (d, J=4.5 Hz).

Intermediate 10

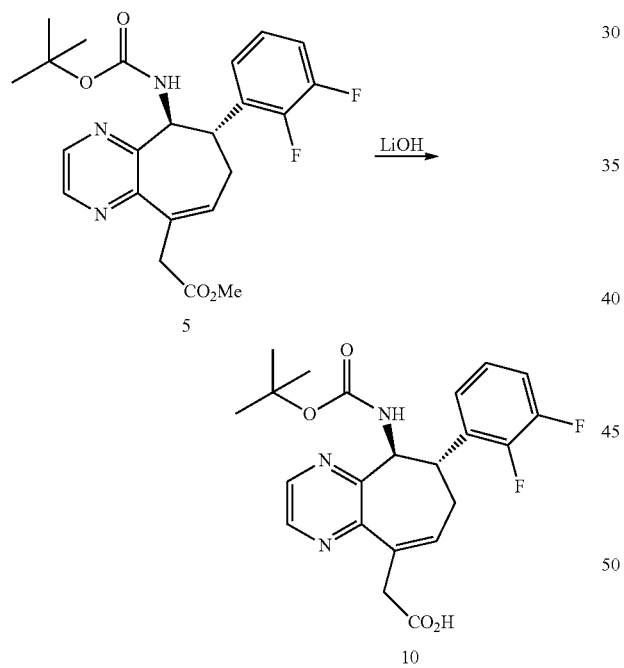

2-((5S,6S,Z)-5-(tert-butoxycarbonylamino)-6-(2,3-difluorophenyl)-6,7-dihydro-5H-cyclohepta[b]pyrazin-9-yl)acetic acid In a 50 mL round-bottomed flask was dissolved methyl 2-((5S,6S)-5-(tert-butoxycarbonylamino)-6-(2,3-difluorophenyl)-6,7-dihydro-5H-cyclohepta[b]pyrazin-9-yl)acetate (5) in 4:1 tetrahydrofuran/methanol (2.5 mL). Lithium hydroxide (0.588 mL, 0.588 mmol) was added and the mixture was stirred at rt for 16 h. LCMS indicated complete conversion. The mixture was concentrated and further dried under a high vacuum to remove water to give a slightly orange solid, which was directly carried on to the next step.

Example 1

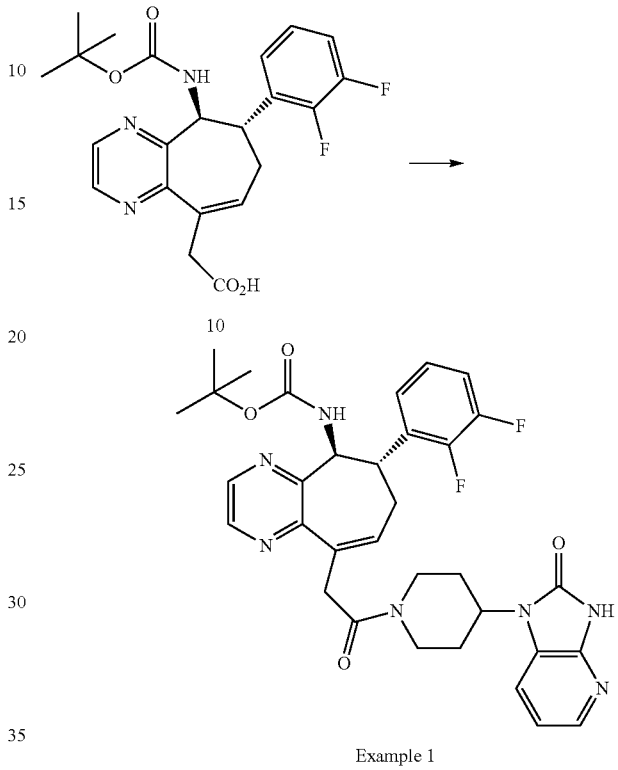

Example 1 tert-butyl (5S,6S,Z)-6-(2,3-difluorophenyl)-9-(2-oxo-2-(4-(2-oxo-2,3-dihydro-1H-imidazo[4,5-b]pyridin-1-yl)piperidin-1-yl)ethyl)-6,7-dihydro-5H-cyclohepta[b]pyrazin-5-ylcarbamate In a 100 mL round-bottomed flask was dissolved 2-((5S, 6S)-5-(tert-butoxycarbonylamino)-6-(2,3-difluorophenyl)-6,7-dihydro-5H-cyclohepta[b]pyrazin-9-yl)acetic acid (63.4 mg, 0.147 mmol) (crude 10, azeotroped twice with dry benzene and further dried under high vacuum) and 1-(piperidin-4-yl)-1H-imidazo[4,5-b]pyridin-2(3H)-one (96 mg, 0.441 mmol) (bis-HCl salt) in methylene chloride (2 mL) to give a colorless suspension. Hunig's base (0.128 mL, 0.735 mmol) and 3-(diethoxyphosphoryloxy)-1,2,3-benzo-triazin-4(3H)-one (88 mg, 0.29 mmol) were added. The reaction mixture was diluted with dimethylformamide (0.5 mL) The mixture was stirred at rt overnight. LCMS indicated complete conversion. It was diluted with ethyl acetate and washed with water and 0.5N sodium hydroxide. The organic layer was washed with brine, dried with sodium sulfate, and concentrated to give a tan oil. Purification by flash column chromatography CISCO) up to 10% methanol in methylene chloride afforded the desired product (59.6 mg, 64%) as a greenish solid: $^1$H NMR (400 MHz, CDCl$_3$) 11.29 (s, 1H), 8.53 (s, 1H), 8.47 (d, J=2.5 Hz, 1H), 8.08 (d, J=5.2 Hz, 1H), 7.45 (d, J=8.1 Hz, 1H), 7.28-7.17 (m, 1H), 7.15-6.94 (m, 3H), 6.61 (dd, J=15.2, 9.3 Hz, 1H), 6.55-6.40 (m, 1H), 5.51 (q, J=8.6 Hz, 1H), 4.85 (d, J=12.2 Hz, 1H), 4.59 (s, 1H), 4.22 (s, 1H), 4.07-3.85 (m, 2H), 3.76 (d, J=16.2 Hz, 1H), 3.28 (t, J=12.0 Hz, 1H), 2.71 (t, J=12.3 Hz, 1H), 2.50-2.08 (m, 4H), 2.02-1.83 (m, 2H), 1.27 (s, J=2.3 Hz, 9H).

Example 2

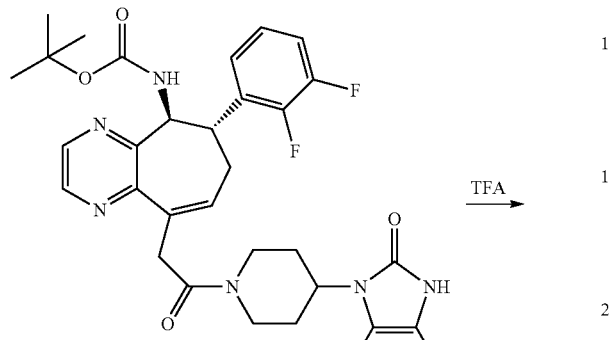

Example 1

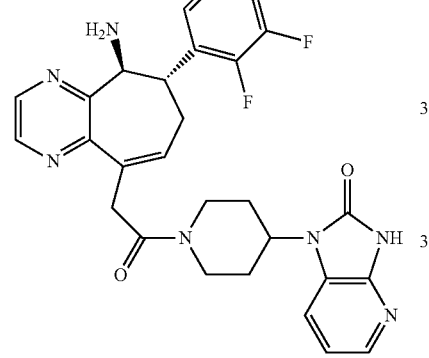

Example 2

1-(1-(2-((5S,6S,Z)-5-amino-6-(2,3-difluorophenyl)-6,7-dihydro-5H-cyclohepta[b]pyrazin-9-yl)acetyl)piperidin-4-yl)-1H-imidazo[4,5-b]pyridin-2(3H)-one In a 50 mL round-bottomed flask was dissolved tert-butyl (5S,6S)-6-(2,3-difluorophenyl)-9-(2-oxo-2-(4-(2-oxo-2,3-dihydro-1H-imidazo[4,5-b]pyridin-1-yl)piperidin-1-yl)ethyl)-6,7-dihydro-5H-cyclohepta[b]pyrazin-5-ylcarbamate (58.6 mg, 0.093 mmol) in methylene chloride (1 mL). trifluoroacetic acid (0.5 mL) was added, and the mixture was stirred at rt for 1 h. LCMS showed complete conversion. Volatile components were removed in vacuo, and the residue was partitioned between ethyl acetate/0.5N sodium hydroxide/saturated sodium bicarbonate solution. The layers were separated. The organic layer was dried and concentrated to give a tan oil. flash column chromatography up to 10% methanol (2M ammonia) in methylene chloride afforded the desired product (36 mg, 73%) as a tan solid: MS (ESI)[M+H$^+$]= 532.3; $^1$H NMR (400 MHz, CDCl$_3$) δ 8.47 (ddd, J=11.4, 8.1, 2.5 Hz, 2H), 8.07 (d, J=5.1 Hz, 1H), 7.46 (t, J=6.7 Hz, 1H), 7.30 (d, J=7.9 Hz, 1H), 7.20 (d, J=7.1 Hz, 1H), 7.08 (dt, J=14.8, 7.7 Hz, 2H), 6.99 (td, J=8.2, 5.3 Hz, 2H), 6.41 (dt, J=22.6, 7.2 Hz, 1H), 4.90-4.68 (m, 2H), 4.56 (dd, J=17.3, 12.7 Hz, 1H), 4.15 (ddd, J=24.9, 20.2, 15.2 Hz, 2H), 3.83 (dt, J=7.2, 6.4 Hz, 1H), 3.64 (dd, J=33.2, 16.2 Hz, 1H), 3.26 (t, J=13.1 Hz, 1H), 2.69 (dd, J=28.5, 13.4 Hz, 1H), 2.39 (d, J=6.8 Hz, 2H), 2.33-2.05 (m, 3H), 2.03-1.69 (m, 2H); 19F NMR (376 MHz, CDCl3) δ −137.26−−138.00 (m), −142.22 (dd, J=96.1, 21.6 Hz).

Example 3

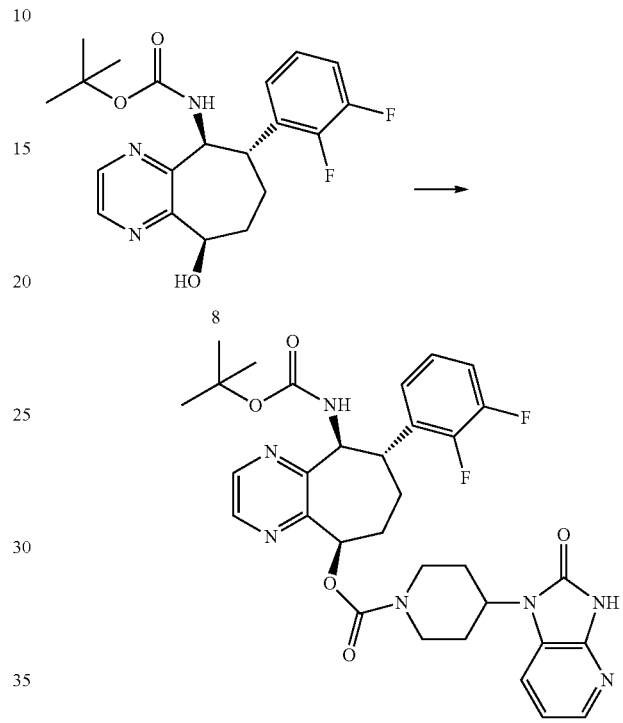

Example 3

(5R,8S,9S)-9-(tert-butoxycarbonylamino)-8-(2,3-difluorophenyl)-6,7,8,9-tetrahydro-5H-cyclohepta[b]pyrazin-5-yl 4-(2-oxo-2,3-dihydro-1H-imidazo[4,5-b]pyridin-1-yl)piperidine-1-carboxylate In a 100 mL round-bottomed flask was dissolved tert-butyl (5S,6S,9R)-6-(2,3-difluorophenyl)-9-hydroxy-6,7,8,9-tetrahydro-5H-cyclohepta[b]pyrazin-5-ylcarbamate (40 mg, 0.102 mmol) (azeotroped with dry benzene) and 1-(1-(1H-imidazole-1-carbonyl)piperidin-4-yl)-1H-imidazo[4,5-b]pyridin-2(3H)-one (41.5 mg, 0.133 mmol) in dimethylformamide (1 mL) to give a colorless suspension under nitrogen. After cooling to −15° C. (ice/methanol bath), NaI-RN/IDS (0.378 mL, 0.378 mmol) was added dropwise. The cooling bath was removed and the resulting tan solution was stirred under nitrogen at rt for 2 h. LCMS showed complete conversion. The reaction was quenched with sodium bicarbonate solution, and diluted with ethyl acetate. The layers were separated. The organic layer was washed with brine, dried with sodium sulfate, and concentrated to give a slightly tan oil. Purification by flash column chromatography up to 10% methanol (with 2M ammonia)/methylene chloride afforded the desired product (39.5 mg, 61%) as a white solid: 1H NMR (400 MHz, CDCl3) δ 11.17 (s, 1H), 8.53 (s, 1H), 8.49 (s, 1H), 8.12 (d, J=5.0 Hz, 1H), 7.43 (d, J=6.0 Hz, 1H), 7.33-7.26 (m, 1H), 7.05 (dt, J=7.8, 5.9 Hz, 3H), 6.34 (d, J=8.8 Hz, 1H), 6.15 (d, J=11.0 Hz, 1H), 5.36-5.25 (m, 1H), 4.63 (t, J=12.4 Hz, 2H), 4.46 (s, 1H), 3.07 (t, J=9.7 Hz, 3H), 2.62 (dd, J=23.9, 11.8 Hz, 1H), 2.49-2.26 (m, 3H), 2.21 (d, J=12.0 Hz, 1H), 2.03-1.78 (m, 3H), 1.23 (s, 9H).

3.31-2.81 (m, 3H), 2.37 (dd, J=23.5, 13.6 Hz, 4H), 2.17-1.67 (m, 6H); 19F NMR (376 MHz, CDCl3) δ −137.10-−137.50 (m), −142.45 (d, J=20.6 Hz).

Example 4

Intermediate 11

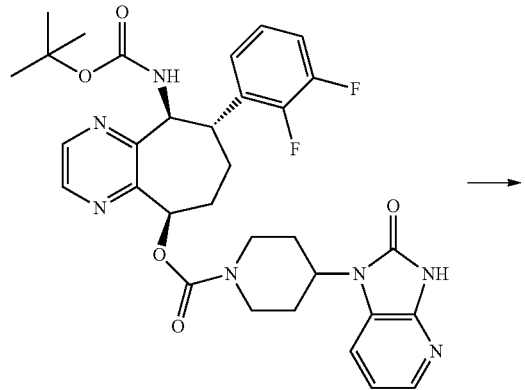

Example 3

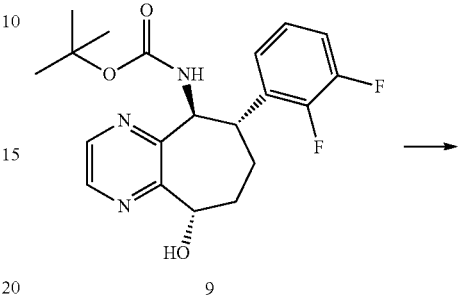

9

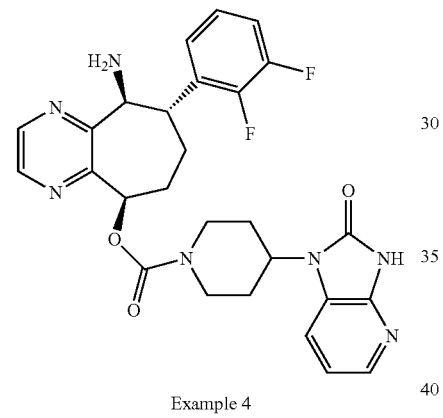

Example 4

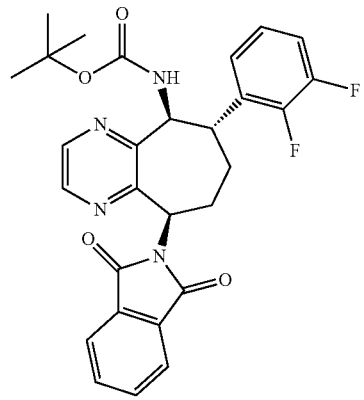

11

(5R,8S,9S)-9-amino-8-(2,3-difluorophenyl)-6,7,8,9-tetrahydro-5H-cyclohepta[b]pyrazin-5-yl 4-(2-oxo-2,3-dihydro-1H-imidazo[4,5-b]pyridin-1-yl)piperidine-1-carboxylate In a 50 mL round-bottomed flask was dissolved (5R,8S,9S)-9-(tert-butoxycarbonylamino)-8-(2,3-difluorophenyl)-6,7,8,9-tetrahydro-5H-cyclohepta[b]pyrazin-5-yl 4-(2-oxo-2,3-dihydro-1H-imidazo[4,5-b]pyridin-1-yl)piperidine-1-carboxylate (38.1 mg, 0.060 mmol) in methylene chloride (1 mL) to give a colorless solution. trifluoroacetic acid (0.5 mL) was added, and the mixture was stirred at rt for 1 h. LCMS showed complete conversion. Volatiles were removed in vacuo, and the residue was partitioned between ethyl acetate/0.5N sodium hydroxide/saturated sodium bicarbonate solution. The layers were separated. The organic layer was dried and concentrated to give a tan oil. flash column chromatography up to 10% methanol (2M ammonia) in methylene chloride afforded the desired product (22 mg, 69%) as a white solid: MS (ESI)[M+H+]=536.2; 1H NMR (400 MHz, CDCl3) δ 8.50 (s, 2H), 8.11 (d, J=4.9 Hz, 1H), 7.42 (s, J=16.5 Hz, 1H), 7.17-6.95 (m, 4H), 6.24-5.97 (m, 2H), 4.69-4.34 (m, 4H), tert-butyl (5S,6S,9R)-6-(2,3-difluorophenyl)-9-(1,3-dioxoisoindolin-2-yl)-6,7,8,9-tetrahydro-5H-cyclohepta[b]pyrazin-5-ylcarbamate In an oven-dried 100 mL round-bottomed flask was dissolved tert-butyl (5S,6S,9S)-6-(2,3-difluorophenyl)-9-hydroxy-6,7,8,9-tetrahydro-5H-cyclohepta[b]pyrazin-5-ylcarbamate (35.3 mg, 0.090 mmol) (9, azeotroped with dry benzene) in methylene chloride (3 mL) to give a colorless solution. isoindoline-1,3-dione (26.5 mg, 0.180 mmol) and triphenylphosphine (47.3 mg, 0.180 mmol) were added, followed by diisopropylazodicarboxylate (0.026 mL, 0.135 mmol). The mixture was stirred at rt under nitrogen. After 22 h, the mixture was directly subject to flash column chromatography up to 50% ethyl acetate/hexane afforded one major peak. Concentration afforded the desired product as a colorless oil. 1H NMR indicated that some elimination product might also be present. This was carried onto next reaction without further purification and characterization.

Intermediate 12

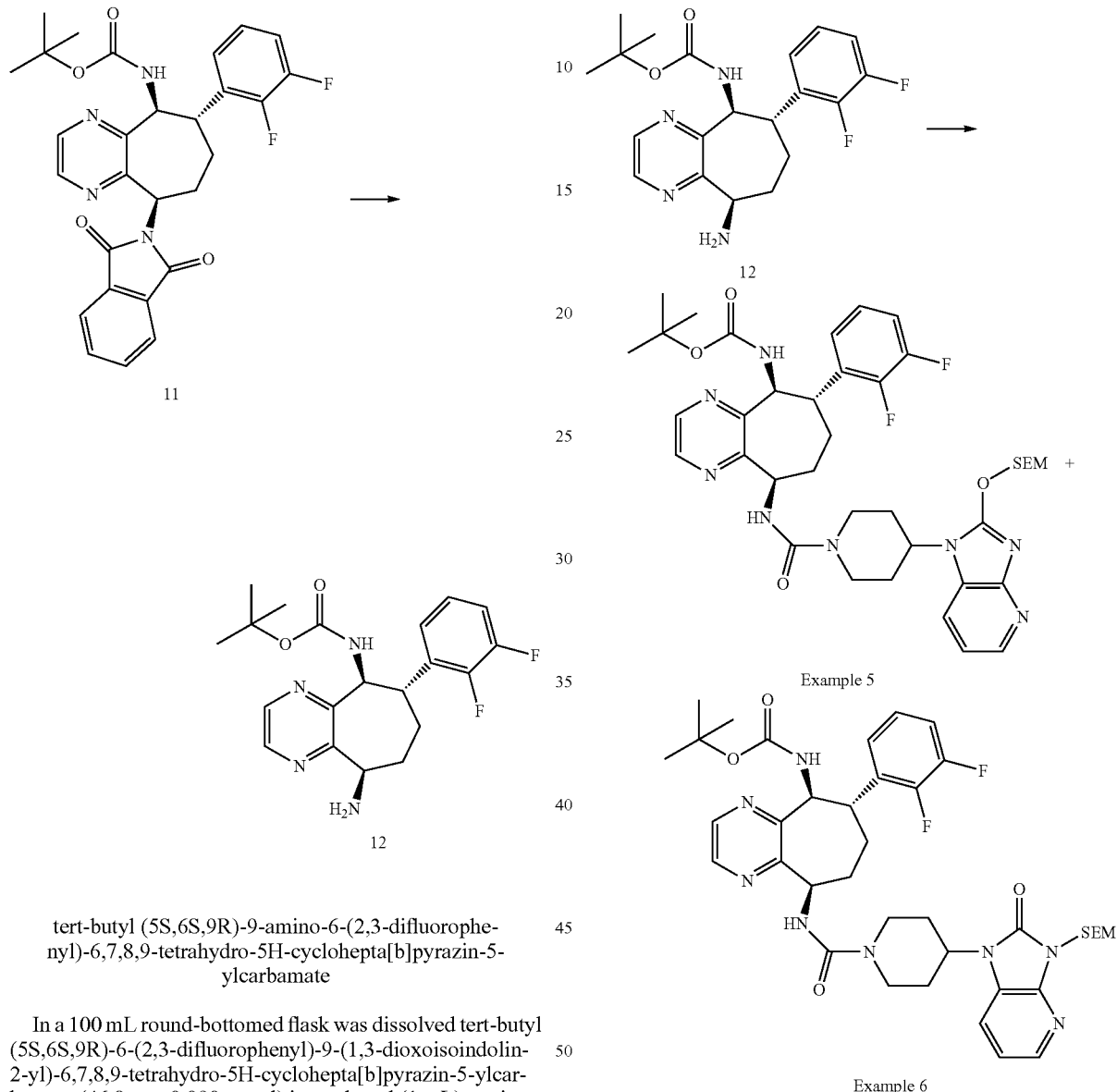

Example 5

Example 6 tert-butyl (5S,6S,9R)-9-amino-6-(2,3-difluorophenyl)-6,7,8,9-tetrahydro-5H-cyclohepta[b]pyrazin-5-ylcarbamate In a 100 mL round-bottomed flask was dissolved tert-butyl (5S,6S,9R)-6-(2,3-difluorophenyl)-9-(1,3-dioxoisoindolin-2-yl)-6,7,8,9-tetrahydro-5H-cyclohepta[b]pyrazin-5-ylcarbamate (46.8 mg, 0.090 mmol) in methanol (1 mL) to give a white suspension. Hydrazine hydrate (0.1 mL, 3.2 mmol) was added, and the mixture was stirred in a preheated oil bath at 70° C. under nitrogen for 2 h. LCMS indicated the desired product. Methanol was removed in vacuo and the residue was partitioned between 0.5N sodium hydroxide and ethyl acetate. The layers were separated and the aqueous layer was extracted with ethyl acetate. The combined organic layers were washed with brine, dried, and concentrated. Flash column chromatography upto 10% methanol (with 2M ammonia) in methylene chloride afforded the desired product as a colorless oil (26.9 mg, 77% for two steps): 1H NMR (400 MHz, CDCl3) δ 8.48 (d, J=2.3 Hz, 1H), 8.42 (d, J=2.4 Hz, 1H), 7.25 (t, J=6.4 Hz, 1H), 7.12-6.98 (m, 2H), 6.24 (d, J=8.6 Hz, 1H), 5.25 (t, J=9.5 Hz, 1H), 4.50 (d, J=10.2 Hz, 1H), 3.03 (t, J=10.7 Hz, 1H), 2.60-2.43 (m, 1H), 2.39-2.07 (m, 4H), 1.61-1.40 (m, 1H), 1.23 (s, 9H); 19F NMR (376 MHz, CDCl3) δ −138.95--139.53 (m), −142.46 (d, J=18.8 Hz).

Examples 5 and 6 tert-butyl (5S,6S,9R)-6-(2,3-difluorophenyl)-9-(4-(2-((2-(trimethylsilyl)ethoxy)methoxy)-1H-imidazo[4,5-b]pyridin-1-yl)piperidine-1-carboxamido)-6,7,8,9-tetrahydro-5H-cyclohepta[b]pyrazin-5-ylcarbamate (example 5) and tert-butyl (5S,6S,9R)-6-(2,3-difluorophenyl)-9-(4-(2-oxo-3-((2-(trimethylsilyl)ethoxy)methyl)-2,3-dihydro-1H-imidazo[4,5-b]pyridin-1-yl)piperidine-1-carboxamido)-6,7,8,9-tetrahydro-5H-cyclohepta[b]pyrazin-5-ylcarbamate (example 6)

In an oven-dried 100 mL round-bottomed flask was dissolved 1-(piperidin-4-yl)-3-((2-(trimethylsilyl)ethoxy)methyl)-1H-imidazo[4,5-b]pyridin-2(3H)-one (36.0 mg, 0.103 mmol) in methylene chloride (2 mL) to give a colorless solution. Triethylamine (0.029 mL, 0.207 mmol) was added under nitrogen and the mixture was cooled to −20° C. Trichloromethyl chloroformate (8 μl, 0.07 mmol) was added dropwise. The mixture was gradually warmed up with stirring to 10° C. for 1 h, during which time the solution became slightly yellow. The mixture was concentrated to dryness under house vacuum and further dried under high vacuum. Tert-butyl (5S, 6S,9R)-9-amino-6-(2,3-difluorophenyl)-6,7,8,9-tetrahydro-5H-cyclohepta[b]pyrazin-5-ylcarbamate (26.9 mg, 0.069 mmol) and triethylamine (0.029 mL, 0.207 mmol) dissolved in 1 mL tetrahydrofuran was added via cannula at rt. The resulting faint yellow suspension was stirred under nitrogen for 3 days. The residue was partitioned between ethyl acetate/0.5 N sodium hydroxide. The organic layer was separated. TLC (10%-methanol/methylene chloride) showed two spots: a less polar dark spot and a faint, more polar blue spot. The organic layer was separated and washed with brine, dried with sodium sulfate, and concentrated. The residue was purified by flash column chromatography up to 10% methanol/methylene chloride afforded two products Example 6 (32 mg, 61%) and Example 5 (7.0 mg, 13%). Example 6: MS (ESI)[M+H$^+$] =765.5; 1H NMR (400 MHz, CDCl$_3$) δ 8.50 (d, J=2.4 Hz, 1H), 8.43 (d, J=2.6 Hz, 1H), 8.07 (dd, J=5.2, 1.2 Hz, 1H), 7.34 (dd, J=7.9, 1.2 Hz, 1H), 7.28 (s, J=5.2 Hz, 1H), 7.11-6.94 (m, 4H), 6.14 (d, J=9.2 Hz, 1H), 5.43 (s, J=3.6 Hz, 2H), 5.40-5.32 (m, 2H), 4.63 (tt, J=12.4, 3.9 Hz, 1H), 4.33 (t, J=13.9 Hz, 2H), 3.77-3.69 (m, 2H), 3.13-2.94 (m, 3H), 2.69 (dd, J=25.5, 13.2 Hz, 1H), 2.57 (d, J=13.5 Hz, 1H), 2.30 (qd, J=12.4, 4.1 Hz, 2H), 2.14 (ddd, J=8.4, 5.0, 2.5 Hz, 1H), 1.95 (d, J=12.2 Hz, 1H), 1.88 (s, 1H), 1.43 (dd, J=23.7, 11.0 Hz, 1H), 1.23 (s, 9H), 1.03-0.95 (m, 2H), −0.02 (s, 9H); 19F NMR (376 MHz, CDCl3) δ −139.05-−139.63 (m), −142.98 (s). Example 5: MS (ESI)[M+H$^+$]=765.5; 1H NMR (400 MHz, CDCl3) δ 8.51 (d, J=2.3 Hz, 1H), 8.45 (d, J=2.6 Hz, 1H), 7.40 (dd, J=6.9, 0.7 Hz, 1H), 7.38-7.29 (m, 1H), 7.12-6.99 (m, 4H), 6.67 (t, J=7.1 Hz, 1H), 6.13 (d, J=9.1 Hz, 1H), 5.74 (s, 2H), 5.37 (t, J=9.3 Hz, 2H); 4.76-4.55 (m, 1H), 4.42-4.23 (m, 2H), 3.73-3.65 (m, 2H), 3.14-2.94 (m, 3H), 2.79-2.63 (m, 1H), 2.58 (d, 0.1-13.6 Hz, 1H), 2.36-2.09 (m, 2H), 1.97 (s, 2H), 1.75 (s, 1H), 1.52-1.36 (m, 1H), 1.24 (s, 9H), 1.01-0.93 (m, 2H), −0.00 (s, 9H); 19F NMR (376 MHz, CDCl3) δ −139.38 (d, J=17.6 Hz), −142.93 (s).

Example 7

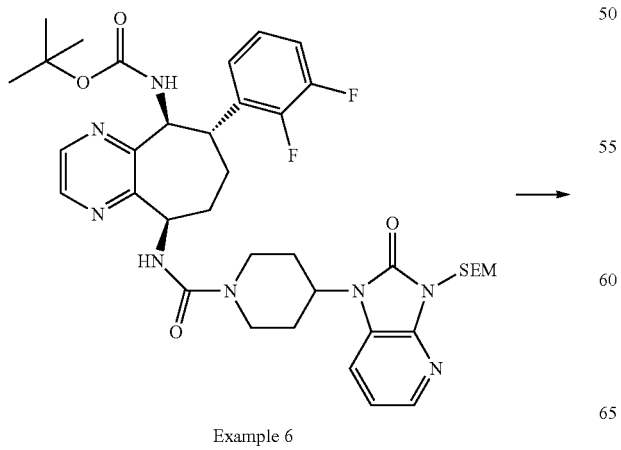

Example 6

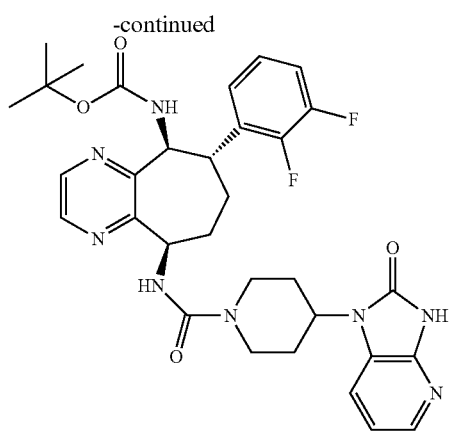

Example 7

N-((5R,8S,9S)-9-amino-8-(2,3-difluorophenyl)-6,7,8,9-tetrahydro-5H-cyclohepta[b]pyrazin-5-yl)-4-(2-oxo-2,3-dihydro-1H-imidazo[4,5-b]pyridin-1-yl)piperidine-1-carboxamide In a 50 mL round-bottomed flask was dissolved tert-butyl (5S,6S,9R)-6-(2,3-difluorophenyl)-9-(4-(2-oxo-3-((2-(trimethylsilyl)ethoxy)methyl)-2,3-dihydro-1H-imidazo[4,5-b]pyridin-1-yl)piperidine-1-carboxamido)-6,7,8,9-tetrahydro-5H-cyclohepta[b]pyrazin-5-ylcarbamate (31 mg, 0.041 mmol) in methylene chloride (1 mL) to give a colorless solution. trifluoroacetic acid (0.5 mL) was added, and the mixture was stirred at rt for 1.5 h: LCMS showed complete conversion. The solvent was removed in vacuo, and the residue was partitioned between ethyl acetate/0.5N sodium hydroxide/saturated sodium bicarbonate solution. The layers were separated. The organic layer was dried and concentrated to give a tan oil. flash column chromatography up to 10% methanol (2M ammonia) in methylene chloride afforded the desired product (12 mg, 55%) as a white solid: MS (ESI) [M+H]$^+$= 535.3; $^1$H NMR (400 MHz, CDCl3) δ 10.98-9.87 (m, 1H), 8.56 (d, J=2.5 Hz, 1H), 8.42 (d, J=2.5 Hz, 1H), 8.07 (dd, J=5.3, 1.2 Hz, 1H), 7.35 (dd, J=7.9, 1.2 Hz, 1H), 7.21-7.05 (m, 4H), 6.98 (dd, J=7.9, 5.3 Hz, 1H), 5.29 (dd, J=10.4, 5.1 Hz, 1H), 4.71-4.55 (m, 2H), 4.35 (d, J=13.6 Hz, 2H), 3.05 (1, J=13.0 Hz, 2H), 2.94 (t, J=9.3 Hz, 1H), 2.53 (t, J=11.7 Hz, 2H), 2.41-2.23 (m, 2H), 2.16-1.69 (m, 6H); 19F NMR (376 MHz, CDCl3) δ −137.32 (ddd, J=21.4, 9.6, 4.5 Hz), −142.66 (d, J=19.5 Hz).

Intermediate 13

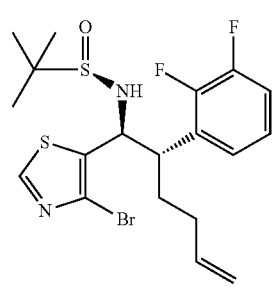

(R)—N-((1S,2S)-1-(4-bromothiazol-5-yl)-2-(2,3-difluorophenyl)hex-5-enyl)-2-methylpropane-2-sulfinamide To a 250 mL round bottom flask was added tetrahydrofuran (10 mL) and diisopropylamine (1.04 mL, 7.33 mmol) under nitrogen. The flask was cooled down to −20° C. before addition of n-BuLi (2.93 mL, 7.33 mmol). The reaction was stirred at this temperature for 5 min before being cooled to −78° C. 2,4-dibromothiazole (1.782 g, 7.33 mmol) was added at once to the reaction mixture. After stirring at −78° C. for 10 min, (R,E)-N-((S)-2-(2,3-difluorophenyl)hex-5-enylidene)-2-methylpropane-2-sulfinamide (1.1494 g, 3.67 mmol) in 5 mL tetrahydrofuran was added to the reaction mixture via cannula. The reaction was allowed to continue to stir while it was gradually warmed up to −60° C. (4 h). The reaction was cooled down to −78° C. and n-BuLi (2.93 mL, 7.33 mmol) was added at −78° C. The reaction was stirred for 20 min. Methanol (0.44 mL, 11.0 mmol)l was added to quench the reaction. The reaction was stirred at rt for 0.5 h. The solvent was removed under vacuum and the crude mixture was partitioned between ethyl acetate and water. The ethyl acetate layer was separated, dried (sodium sulfate), filtered and concentrated. Flash chromatography using ethyl acetate in hexane from 0 to 50% to 85% gave the desired product (1.08 g, 62%) as a brown oil, which was solidified upon standing at room temperature overnight: MS (ESI)[M+H$^+$]=479.12. 1H NMR showed a mixture of two diastereomers with a ratio of 3/1 (epimerized 1 from previous reactions).

Intermediate 14

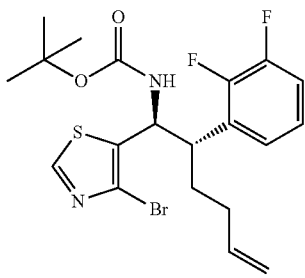

14 tert-butyl (1S,2S)-1-(4-bromothiazol-5-yl)-2-(2,3-difluorophenyl)hex-5-enylcarbamate 2M HCl in diethyl ether (4.82 mL, 9.63 mmol) was added to a methanol (10 mL) solution of (R)—N-((1S,2S)-1-(4-bromothiazol-5-yl)-2-(2,3-difluorophenyl)hex-5-enyl)-2-methylpropane-2-sulfinamide (1.15 g, 2.409 mmol) at rt. The reaction was stirred for 2.5 h before removal of the solvent. The crude mixture was partitioned between ethyl acetate and saturated sodium bicarbonate. The ethyl acetate layer was separated, dried (sodium sulfate), filtered and concentrated. Flash chromatography using ethyl acetate in hexane from 0 to 45% to 65% gave the desired free amine intermediate: MS (ESI) [M+H$^+$]=375.08. 1H NMR showed inseparable diastereomers with a ratio of 3:1.
(1S,2S)-1-(4-bromothiazol-5-yl)-2-(2,3-difluorophenyl)hex-5-en-1-amine (600 mg, 1.607 mmol) was dissolved in methylene chloride (10 mL). Boc$_2$O (3.5 g) was added to the reaction mixture at rt. The reaction was put in the refrigerator overnight. The solvent was removed and the crude mixture was purified by silica gel flash chromatography, eluting with ethyl acetate in hexane from 0 to 45% to afford the desired product (722 mg, 95%): MS (ESI)[M+H$^+$]=475.10. 1H NMR showed inseparable diastereomers with a ratio of 3/1.

Intermediate 15

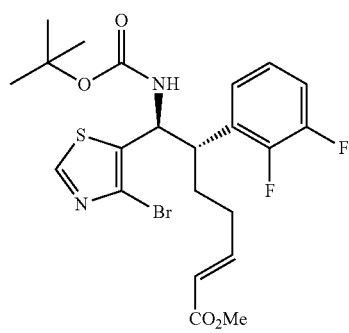

15

(6S,7S,E)-methyl 7-(4-bromothiazol-5-yl)-7-(tert-butoxycarbonylamino)-6-(2,3-difluorophenyl)hept-2-enoate A mixture of methyl acrylate (0.16 mL, 1.80 mmol), GrubbsII catalyst (0.025 g, 0.030 mmol) and tert-butyl (1S,2S)-1-(4-bromothiazol-5-yl)-2-(2,3-difluorophenyl)hex-5-enylcarbamate (0.2842 g, 0.600 mmol) in methylene chloride (20 mL) was heat to reflux for 3 h under nitrogen. The solvent was removed under vacuum and the crude product was purified by silica gel chromatography, eluting with ethyl acetate in hexane from 0 to 45% to give the desired product (273.2 mg, 86%): MS (ESI)[M+H$^+$]=533.13. 1H NMR showed inseparable diastereomers with a ratio of 3.5:1.

Intermediate 16

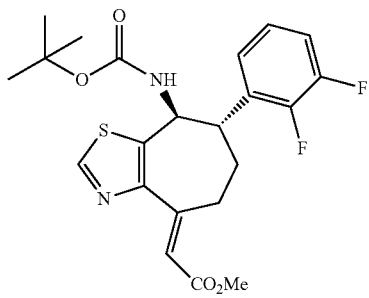

16

(E)-methyl 2-((7S,8S)-8-(tert-butoxycarbonylamino)-7-(2,3-difluorophenyl)-5,6,7,8-tetrahydro-4H-cyclohepta[d]thiazol-4-ylidene)acetate A mixture of (6S,7S,E)-methyl 7-(4-bromothiazol-5-yl)-7-(tert-butoxycarbonylamino)-6-(2,3-difluorophenyl)hept-2-enoate (0.217 g, 0.409 mmol), bis(tri-t-butylphosphine) palladium (0) (0.021 g, 0.041 mmol) and methyl dicyclohexylamine (0.096 mL, 0.450 mmol) in dioxane (10 mL) (degassed with nitrogen) was heated at 140° C. under microwave radiation for 1 h under nitrogen. The solvent was removed under vacuum and the product was purified by flash chromatography eluting with ethyl acetate in hexane from 0 to 45% to afford the desired product (53.4 mg, 29%), (M+H=451.20), as well as the isomerized product (double bond moved into the ring) (108.8 mg, 59%) as the major component.

Intermediate 17

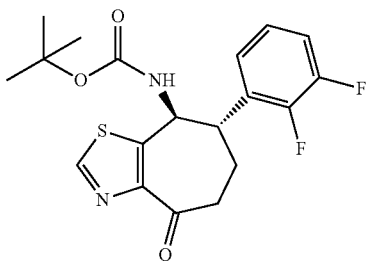

tert-butyl (7S,8S)-7-(2,3-difluorophenyl)-4-oxo-5,6,7,8-tetrahydro-4H-cyclohepta[d]thiazol-8-ylcarbamate A solution of (E)-methyl 2-((7S,8S)-8-(tert-butoxycarbonylamino)-7-(2,3-difluorophenyl)-5,6,7,8-tetrahydro-4H-cyclohepta[d]thiazol-4-ylidene)acetate (68 mg, 0.15 mmol) in methylene chloride (5 mL) was treated with ozone under −78° C. for 2 min. The reaction mixture was purged with nitrogen and quenched with dimethyl sulfide. The solvent was removed under vacuum and the product was purified by flash chromatography, eluting with ethyl acetate in hexane from 0 to 100% to afford the desired product (34.5 mg, 58%): $^1$H NMR (400 MHz, CHLOROFORM-d) δ 8.73 (s, 1H), 7.16-7.09 (m, 3H), 5.62-5.53 (m, 1H), 5.13-5.05 (m, 1H), 3.64-3.53 (m, 1H), 3.13-3.02 (m, 1H), 3.01-2.92 (m, 1H), 2.38-2.24 (m, 2H), 1.36-1.29 (m, 9H); $^{19}$F NMR (400 MHz, CHLOROFORM-d) δ −137.33, −141.96.

The minor diastereomer (12.1 mg, 20%) was separated at this step: $^1$H NMR (400 MHz, CHLOROFORM-d) δ 8.77 (s, 1H), 7.19-7.09 (m, 1H), 7.05-6.97 (m, 1H), 6.54 (br. s., 1H), 5.84-5.76 (m, 1H), 4.79-4.70 (m, 1H), 4.14 (d, J=7.0 Hz, 1H), 3.08-2.89 (m, 2H), 2.53-2.43 (m, 1H), 2.04-1.92 (m, 1H), 1.44 (s, 9H); $^{19}$F NMR (400 MHz, CHLOROFORM-d) δ −136.00, −141.64.

Intermediate 18

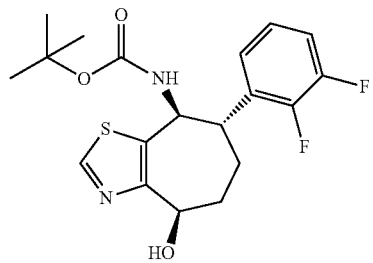

tert-butyl (4R,7S,8S)-7-(2,3-difluorophenyl)-4-hydroxy-5,6,7,8-tetrahydro-4H-cyclohepta[d]thiazol-8-ylcarbamate Sodium borohydride (9.93 mg, 0.262 mmol) was added to a methanol (5 mL) solution of tert-butyl (7S,8S)-7-(2,3-difluorophenyl)-4-oxo-5,6,7,8-tetrahydro-4H-cyclohepta[d]thiazol-8-ylcarbamate (34.5 mg, 0.087 mmol) at rt. The reaction was stirred for 0.5 h. The solvent was removed under vacuum and the product was purified by prep TLC developed with ethyl acetate in hexane (50%). There were two bands collected. The less polar was the desired product (20.1 mg. 58%): LCMS: M+H=397.24; 1H NMR (400 MHz, CHLOROFORM-d) δ ppm 8.57 (1H, s), 7.03-7.09 (3H, m), 5.16-5.23 (1H, m), 4.94-5.00 (1H, m), 4.85-4.91 (1H, m), 4.26 (1H, s), 3.28-3.36 (1H, m), 2.19-2.36 (3H, m), 1.64-1.69 (1H, m), 1.26-1.29 (8H, m).

Intermediate 19

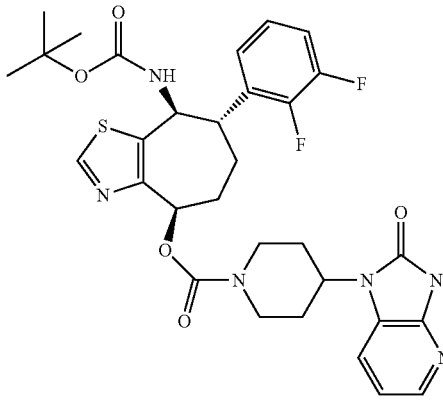

(4R,7S,8S)-8-(tert-butoxycarbonylamino)-7-(2,3-difluorophenyl)-5,6,7,8-tetrahydro-4H-cyclohepta[d]thiazol-4-yl 4-(2-oxo-2,3-dihydro-1H-imidazo[4,5-b]pyridin-1-yl)piperidine-1-carboxylate NaHMDS (0.228 mL, 0.228 mmol) was added to a dimethylformamide (1 mL) solution of tert-butyl (4R,7S,8S)-7-

(2,3-difluorophenyl)-4-hydroxy-5,6,7,8-tetrahydro-4H-cyclohepta[d]thiazol-8-ylcarbamate (20.1 mg, 0.051 mmol) and 1-(1-(1H-imidazole-1-carbonyl)piperidin-4-yl)-1H-imidazo[4,5-b]pyridin-2(3H)-one (23.7 mg, 0.076 mmol) at 0° C. The reaction was stirred at 0° C. for 1 h and rt for 2 h before quenching with water. The reaction was diluted with ethyl acetate and the organic layer was separated, washed with water and brine and then dried (sodium sulfate), filtered and concentrated. Flash chromatography, eluting with methanol in methylene chloride from 0 to 10% gave the desired product (18.2 mg, 56%): LCMS (M+H=641.38); $^1$H NMR (400 MHz, CHLOROFORM-d) δ ppm 8.64 (1H, s), 8.07 (1H, d, J=5.0 Hz), 7.31-7.56 (1H, m), 6.93-7.12 (4H, m), 6.22 (1H, d, J=7.5 Hz), 5.24-5.34 (1H, m), 4.96-5.07 (1H, m), 4.32-4.71 (3H, m), 3.61-3.77 (1H, m), 2.88-3.15 (2H, m), 2.29 (4H, d, J=10.5 Hz), 1.83-1.97 (4H, m), 1.30 (9H, s).

Example 8

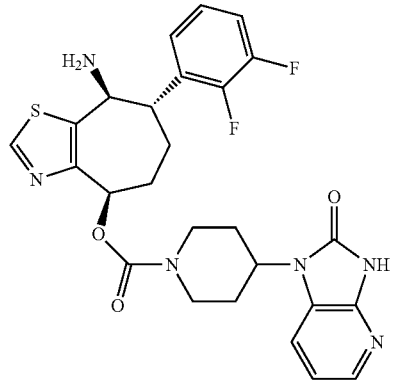

Example 8

(4R,7S,8S)-8-amino-7-(2,3-difluorophenyl)-5,6,7,8-tetrahydro-4H-cyclohepta[d]thiazol-4-yl 4-(2-oxo-2,3-dihydro-1H-imidazo[4,5-b]pyridin-1-yl)piperidine-1-carboxylate A mixture of trifluoroacetic acid (0.986 mL, 12.80 mmol) and (4R,7S,8S)-8-(tert-butoxycarbonylamino)-7-(2,3-difluorophenyl)-5,6,7,8-tetrahydro-4H-cyclohepta[d]thiazol-4-yl 4-(2-oxo-2,3-dihydro-1H-imidazo[4,5-b]pyridin-1-yl)piperidine-1-carboxylate (16.4 mg, 0.026 mmol) in methylene chloride (10 mL) was stirred at rt from for 2.5 h. The solvent was removed under vacuum and the crude product was taken up in ethyl acetate and washed with saturated sodium bicarbonate. The ethyl acetate layer was separated, dried (sodium sulfate), filtered and concentrated. Flash chromatography, eluting with methanol in methylene chloride from 0 to 10% gave the desired product (13 mg, 89%) as a white solid: LCMS (M+H=541.40); $^1$H NMR (400 MHz, CHLOROFORM-d) δ ppm 9.98 (1H, br. s), 8.64 (1H, s), 8.08 (1H, d, J=4.8 Hz), 7.31-7.64 (1H, m), 6.94-7.19 (4H, m), 6.11-6.21 (1H, m), 4.42 (4H, m), 3.23-3.43 (1H, m), 2.85-3.16 (2H, m), 2.24 (6H, m), 1.83-1.98 (2H, m), 1.56 (2H, br.

Intermediate 20

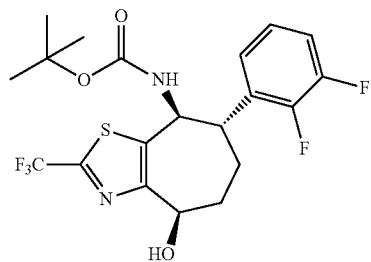

tert-butyl(4R,7S,8S)-7-(2,3-difluorophenyl)-4-hydroxy-2-(trifluoromethyl)-5,6,7,8-tetrahydro-4H-cyclohepta[d]thiazol-8-ylcarbamate Reference: Kino, T.; Nagase, Y.; Ohtsuka, Y.; Yamamoto, K.; Uraguchi, D.; Tokuhisa, K.; Yamakawa, T. *J. Fluorine Chem.* 2010, 131, 98-105.

Trifluoromethyliodide gas was bubbled through 4 mL of dimethylsulfoxide for 3 min at rt. In this way, approximately 0.9 g of trifluoromethyliodide was dissolved in this solution. Dicyclopentadienyliron(II) (21.9 mg, 0.114 mmol) and tert-butyl (4R,7S,8S)-7-(2,3-difluorophenyl)-4-hydroxy-5,6,7,8-tetrahydro-4H-cyclohepta[d]thiazol-8-ylcarbamate (45.3 mg, 0.114 mmol) was dissolved in 2 mL of the trifluoromethyliodide-dimethylsulfoxide solution described above. Hydrogen peroxide (0.012 mL, 0.114 mmol) was added to the reaction mixture. The reaction was stirred at rt for 1 h. Aqueous sodium carbonate was added and the reaction was extracted with ethyl acetate. The ethyl acetate layer was washed with water (2×) and dried (sodium sulfate). The product was purified by flash chromatography, eluting with ethyl acetate in hexane from 0 to 30% to 45% to give the desired product (12.5 mg, 24%): LCMS (M+H=465.08); $^1$H NMR (400 MHz, CHLOROFORM-d) δ 7.21-6.97 (m, 3H), 5.30-5.16 (m, 1H), 498-4.84 (m, 2H), 3.43-3.28 (m, 1H), 3.12-2.79 (m, 2H), 2.43-2.13 (m, 3H), 1.37-1.18 (m, 9H).

Intermediate 21

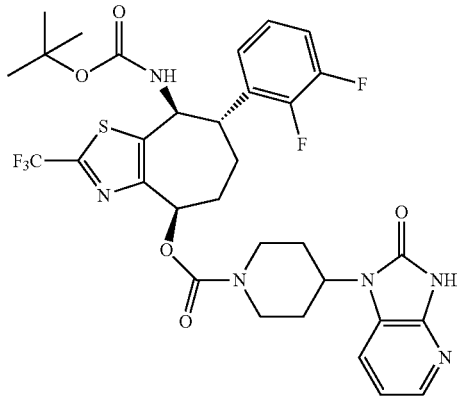

(4R,7S,8S)-8-(tert-butoxycarbonylamino)-7-(2,3-difluorophenyl)-2-(trifluoromethyl)-5,6,7,8-tetrahydro-4H-cyclohepta[d]thiazol-4-yl 4-(2-oxo-2,3-dihydro-1H-imidazo[4,5-b]pyridin-1-yl)piperidine-1-carboxylate NaHMDS (0.1 mL, 0.100 mmol) was added to a dimethylformamide (1 mL) solution of tert-butyl (4R,7S,8S)-7-(2,3-difluorophenyl)-4-hydroxy-2-(trifluoromethyl)-5,6,7,8-tetrahydro-4H-cyclohepta[d]thiazol-8-ylcarbamate (12.5 mg, 0.027 mmol) and 1-(1-(1H-1-imidazole-1-carbonyl)piperidin-4-yl)-1H-imidazo[4,5-b]pyridin-2(3H)-one (12.61 mg, 0.040 mmol) at −20° C. The reaction was stirred at −20° C. for 1 h and rt for 2 h before being quenched with water. The reaction was diluted with ethyl acetate and the organic layer was separated, washed with water, brine, water, and then dried (sodium sulfate), filtered and concentrated in vacuo. Flash chromatography, eluting with methanol in methylene chloride from 0 to 10% gave the desired product (3.5 mg, 18%): LCMS (M+Na=731.06).

Example 9

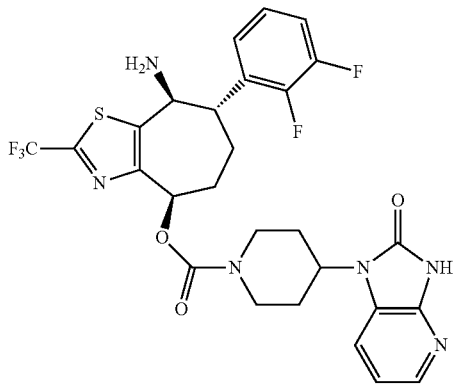

Example 9

(4R,7S,8S)-8-amino-7-(2,3-difluorophenyl)-2-(trifluoromethyl)-5,6,7,8-tetrahydro-4H-cyclohepta[d]thiazol-4-yl 4-(2-oxo-2,3-dihydro-1H-imidazo[4,5-b]pyridin-1-yl)piperidine-1-carboxylate (4R,7S,8S)-8-(tert-butoxycarbonylamino)-7-(2,3-difluorophenyl)-2-(trifluoromethyl)-5,6,7,8-tetrahydro-4H-cyclohepta[d]thiazol-4-yl 4-(2-oxo-2,3-dihydro-1H-imidazo[4,5-b]pyridin-1-yl)piperidine-1-carboxylate (3.5 mg, 4.94 μmol) in methylene chloride (2 mL) was treated with trifluoroacetic acid (0.5 mL, 6.49 mmol) at rt. The reaction was stirred for 2 h. The solvent was removed under vacuum and the crude product was partitioned between sodium bicarbonate(sat.) and ethyl acetate. The organic layer was separated, dried (sodium sulfate), filtered and concentrated in vacuo. Flash chromatography, eluting with methanol in methylene chloride from 0 to 10% gave the desired product (2.7 mg, 90%) as a white solid: LCMS (M+Na=631.04).

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula 1

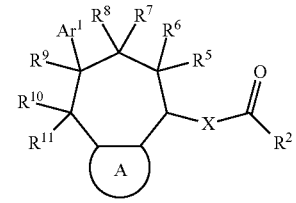

such that ring A is selected from the group consisting of

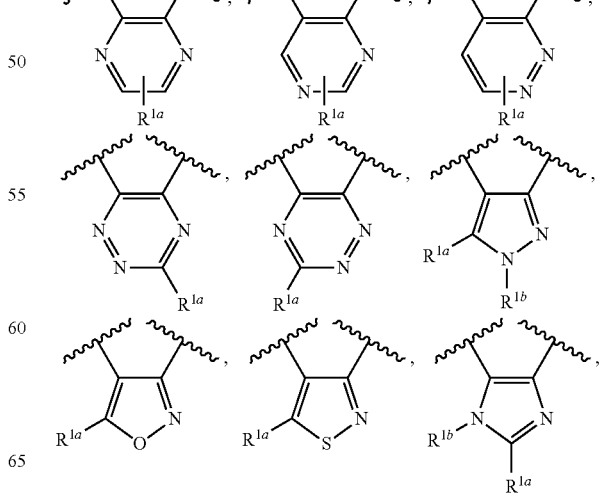

-continued

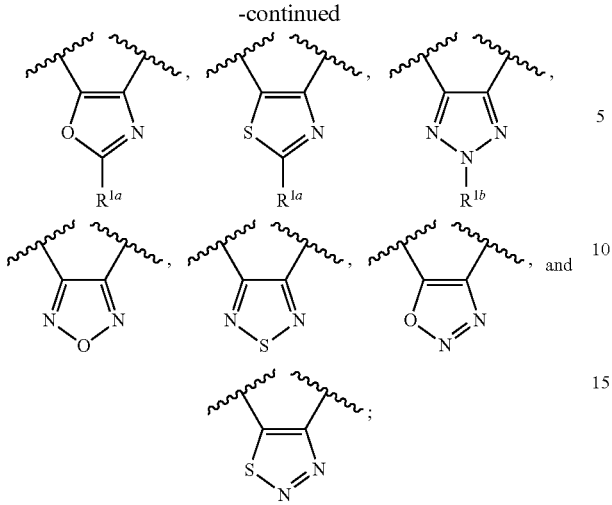

and wherein $R^{1a}$ is hydrogen, cyano, halo, alkyl, haloalkyl, alkoxy, amino, alkylamino, dialkylamino, azetidinyl, pyrrolidinyl, or piperidinyl;

$R^{1b}$ is hydrogen, alkyl, or haloalkyl;

$R^2$ is piperidinyl substituted with 1 substituent selected from the group consisting of

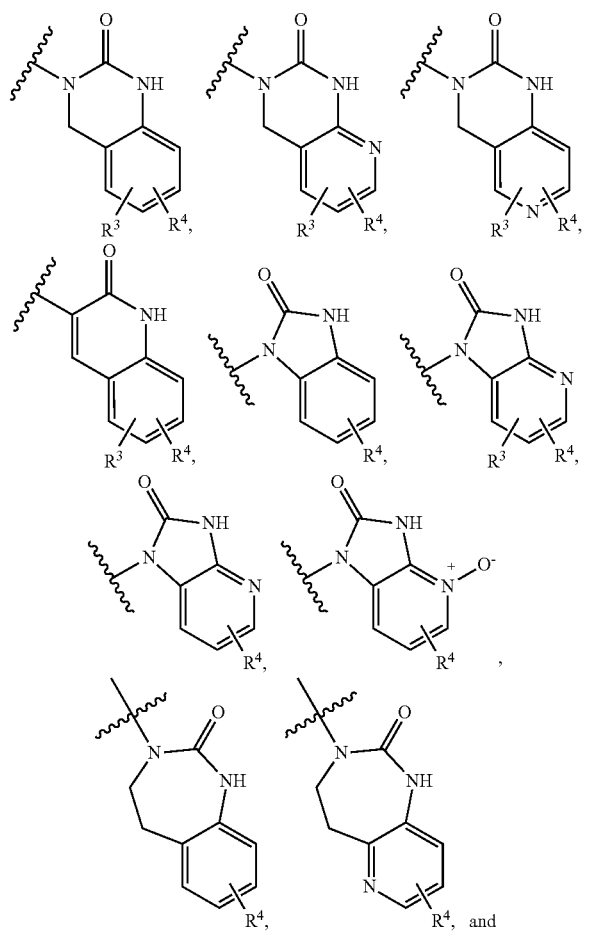

-continued

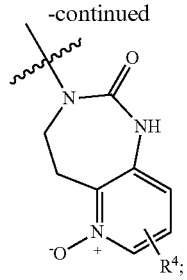

or $R^2$ is

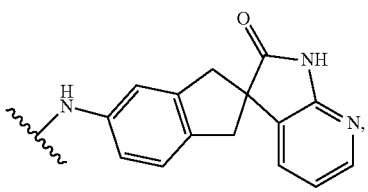

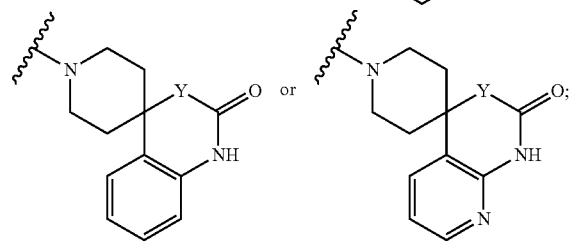

$R^3$ is hydrogen, halo, cyano, alkyl, haloalkyl, alkoxy, or haloalkoxy;

$R^4$ is hydrogen, halo, cyano, alkyl, haloalkyl, alkoxy, or haloalkoxy;

$R^5$ is hydrogen, hydroxy, alkoxy, haloalkoxy, azido, amino, alkylamino, or dialkylamino;

$R^6$ is hydrogen, hydroxy, alkoxy, haloalkoxy, azido, amino, alkylamino, or dialkylamino;

$R^7$ is hydrogen, hydroxy, alkoxy, haloalkoxy, azido, amino, alkylamino, or dialkylamino;

$R^8$ is hydrogen, hydroxy, alkoxy, haloalkoxy, azido, amino, alkylamino, or dialkylamino;

$R^9$ is hydrogen, hydroxy, alkoxy, haloalkoxy, azido, amino, alkylamino, or dialkylamino;

$R^{10}$ is hydrogen, hydroxy, alkoxy, haloalkoxy, azido, amino, alkylamino, dialkylamino, azetidinyl, pyrrolidinyl, piperidinyl, piperazinyl, morpholinyl, alkoxycarbonylamino, or benzyloxycarbonylamino;

$R^{11}$ is hydrogen, hydroxy, alkoxy, haloalkoxy, azido, amino, alkylamino, dialkylamino, azetidinyl, pyrrolidinyl, piperidinyl, piperazinyl, morpholinyl, alkoxycarbonylamino, or benzyloxycarbonylamino;

or $R^{10}$ and $R^{11}$ taken together is O or N—OH;

provided that at least one of $R^5$, $R^6$, $R^7$, $R^8$, $R^9$, $R^{10}$, or $R^{11}$ is not hydrogen;

$Ar^1$ is phenyl substituted with 0-3 substituents selected from the group consisting of cyano, halo, alkyl, haloalkyl, alkoxy, haloalkoxy, and alkylSO$_2$;

X is O, CH$_2$, or NH; and

Y is a bond, O, CH$_2$, or NH;

or a pharmaceutically acceptable salt thereof.

2. A compound of claim 1 with the designated stereochemistry

[structure of substituted cycloheptane ring A with R⁵–R¹¹, Ar¹, X, and C(O)R² substituents]

3. A compound of claim 1 where $R^{1a}$ is hydrogen, alkyl, or haloalkyl;

$R^{1b}$ is hydrogen or alkyl;

$R^2$ is piperidinyl substituted with 1 substituent selected from the group consisting of

[four structures: imidazo-pyridinone with $R^3$; imidazo-pyridinone with $R^3$, $R^4$; benzodiazepinone with $R^3$; and spiropiperidine-benzoxazinone with Y]

$R^3$ is hydrogen or halo;

$R^4$ is hydrogen or halo;

$R^5$ is hydrogen or hydroxy;

$R^6$ is hydrogen;

$R^7$ is hydrogen;

$R^8$ is hydrogen;

$R^9$ is hydrogen or hydroxy;

$R^{10}$ is hydroxy, alkoxy, haloalkoxy, azido, amino, alkylamino, dialkylamino, azetidinyl, pyrrolidinyl, piperidinyl, piperazinyl, morpholinyl, alkoxycarbonylamino, or benzyloxycarbonylamino;

$R^{11}$ is hydrogen;

or $R^{10}$ and $R^{11}$ taken together is oxo;

provided that at least one of $R^5, R^6, R^7, R^8, R^9$, or $R^{11}$ is not hydrogen;

$Ar^1$ is phenyl substituted with 0-2 halo substituents;

X is O, CH₂, or NH; and

Y is O;

or a pharmaceutically acceptable salt thereof.

4. A compound of claim 1 where $R^{a1}$ is hydrogen or haloalkyl; $R^{1b}$ is hydrogen; $R^2$ is piperidinyl substituted with 1 substituent selected from the group consisting of

[four structures: imidazo-pyridinone; dibromo imidazo-pyridinone; benzodiazepinone; spiropiperidine-pyrido-oxazinone]

$R^5$ is hydrogen or hydroxy; $R^6$ is hydrogen; $R^7$ is hydrogen; $R^8$ is hydrogen; $R^9$ is hydrogen or hydroxy; $R^{10}$ is hydroxy, azido, amino, or alkoxycarbonylamino; $R^{11}$ is hydrogen; or $R^{10}$ and $R^{11}$ taken together is oxo; provided that at least one of $R^5, R^6, R^7, R^8, R^9$, or $R^{11}$ is not hydrogen; $Ar^1$ is phenyl or difluorophenyl; X is O, CH₂, or NH; and Y is O; or a pharmaceutically acceptable salt thereof.

5. A compound of claim 1 where ring A is

[two structures: pyrimidine with $R^{1a}$ and thiazole with $R^{1a}$]

6. A compound of claim 1 where $R^2$ is N-piperidinyl and is 4-substituted.

7. A compound of claim 6 where the substituent is

[two structures: imidazo-pyridinone and benzodiazepinone]

8. A compound of claim 1 where $R^5$ is hydrogen, $R^6$ is hydrogen, $R^7$ is hydrogen, $R^8$ is hydrogen, $R^9$ is hydrogen, $R^{10}$ is hydroxy, azido, or amino, and $R^{11}$ is hydrogen; or where $R^5$ is hydrogen, $R^6$ is hydrogen, $R^7$ is hydrogen, $R^8$ is hydrogen, $R^9$ is hydrogen or hydroxy, and $R^{10}$ and $R^{11}$ taken together is oxo; or where $R^5$ is hydrogen, $R^6$ is hydrogen, $R^7$ is hydrogen, $R^8$ is hydrogen, $R^9$ is hydroxy, $R^{10}$ is hydrogen or hydroxy, and $R^{11}$ is hydrogen; or where $R^5$ is hydroxy, $R^6$ is hydrogen, $R^7$ is hydrogen, $R^8$ is hydrogen, $R^9$ is hydrogen, $R^{10}$ is hydrogen, and $R^{11}$ is hydrogen.

9. A compound of claim 1 where $Ar^1$ is phenyl substituted with 2 halo substituents.

10. A compound of claim 9 where $Ar^1$ is 2,3-difluorophenyl.

11. A compound of claim 1 where X is O.

12. A compound of claim 1 selected from the group consisting of
- (5R,8S,9S)-9-(tert-butoxycarbonylamino)-8-(2,3-difluorophenyl)-6,7,8,9-tetrahydro-5H-cyclohepta[b]pyrazin-5-yl 4-(2-oxo-2,3-dihydro-1H-imidazo[4,5-b]pyridin-1-yl)piperidine-1-carboxylate;
- (5R,8S,9S)-9-amino-8-(2,3-difluorophenyl)-6,7,8,9-tetrahydro-5H-cyclohepta[b]pyrazin-5-yl-4-(2-oxo-2,3-dihydro-1H-imidazo[4,5-b]pyridin-1-yl)piperidine-1-carboxylate;
- N-((5R,8S,9S)-9-amino-8-(2,3-difluorophenyl)-6,7,8,9-tetrahydro-5H-cyclohepta[b]pyrazin-5-yl)-4-(2-oxo-2,3-dihydro-1H-imidazo[4,5-b]pyridin-1-yl)piperidine-1-carboxamide;
- (4R,7S,8S)-8-amino-7-(2,3-difluorophenyl)-5,6,7,8-tetrahydro-4H-cyclohepta[d]thiazol-4-yl-4-(2-oxo-2,3-dihydro-1H-imidazo[4,5-b]pyridin-1-yl)piperidine-1-carboxylate; and
- (4R,7S,8S)-8-amino-7-(2,3-difluorophenyl)-2-(trifluoromethyl)-5,6,7,8-tetrahydro-4H-cyclohepta[d]thiazol-4-yl 4-(2-oxo-2,3-dihydro-1H-imidazo[4,5-b]pyridin-1-yl)piperidine-1-carboxylate;

or a pharmaceutically acceptable salt thereof.

13. A composition comprising a compound of claim 1, or a pharmaceutically acceptable salt thereof, and a pharmaceutically acceptable carrier.

14. A method of treating migraine comprising the administration of a therapeutically effective amount of a compound of claim 1, or a pharmaceutically acceptable salt thereof, to a patient.

* * * * *

UNITED STATES PATENT AND TRADEMARK OFFICE
CERTIFICATE OF CORRECTION

PATENT NO. : 8,748,429 B2
APPLICATION NO. : 13/439096
DATED : June 10, 2014
INVENTOR(S) : Guanglin Luo et al.

Page 1 of 1

It is certified that error appears in the above-identified patent and that said Letters Patent is hereby corrected as shown below:

On the Title Page:

Item (75), Inventors:

Change "Gene M. Dubowchik, Middlefleid, CT (US);" to -- Gene M. Dubowchik, Middlefield, CT (US); --.

In the Claims:

Claim 1:

Column 48, line 31, change "Formula 1" to -- Formula I --.

Claim 2:

Column 51, lines 1 and 2, change "stereochemistry" to -- stereochemistry. --.

Claim 4:

Column 51, line 65, change "$R^{a1}$" to -- $R^{1a}$ --.

Signed and Sealed this
Seventh Day of April, 2015

Michelle K. Lee
*Director of the United States Patent and Trademark Office*